US012635887B2

(12) United States Patent
Uchida et al.

(10) Patent No.: US 12,635,887 B2
(45) Date of Patent: May 26, 2026

(54) SYSTEM, INFORMATION STORAGE MEDIUM, AND INFORMATION PROCESSING METHOD

(71) Applicant: OLYMPUS CORPORATION, Tokyo (JP)

(72) Inventors: Takeo Uchida, Kunitachi (JP); Hideyuki Kasahara, Hamura (JP); Yoshitaka Honda, Hachioji (JP); Kazue Tanaka, Sagamihara (JP); Takeshi Arai, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 295 days.

(21) Appl. No.: 18/237,599

(22) Filed: Aug. 24, 2023

(65) Prior Publication Data

US 2023/0404652 A1 Dec. 21, 2023

Related U.S. Application Data

(63) Continuation of application No. PCT/JP2022/009694, filed on Mar. 7, 2022.

(Continued)

(51) Int. Cl.
*A61B 18/12* (2006.01)
*A61B 5/00* (2006.01)
(Continued)

(52) U.S. Cl.
CPC ............ *A61B 5/0093* (2013.01); *A61B 18/04* (2013.01); *A61B 18/1445* (2013.01);
(Continued)

(58) Field of Classification Search
CPC ..... A61B 18/04; A61B 18/1445; A61B 18/12; A61B 2018/00577; A61B 2018/00702;
(Continued)

(56) References Cited

U.S. PATENT DOCUMENTS 8,398,541 B2 3/2013 DiMaio et al.
10,307,209 B1 6/2019 Yu
(Continued)

FOREIGN PATENT DOCUMENTS

EP 3505124 A1 7/2019
EP 3767535 A1 1/2021
(Continued)

OTHER PUBLICATIONS

International Search Report dated May 24, 2022 received in PCT/JP2022/009694.
(Continued)

*Primary Examiner* — Daniel W Fowler

(74) *Attorney, Agent, or Firm* — Scully, Scott, Murphy & Presser, P.C.

(57) ABSTRACT

The system includes a memory that stores a trained model, and a processor. The processor acquires at least one treatment image including an image in which at least one energy device and at least one biological tissue are captured. The processor acquires information regarding an amount of energy supply, the information regarding an energy output setting of the energy device. The processor estimates, based on the treatment image, the information regarding the amount of energy supply, and the trained model, estimated remaining heat information regarding an amount of heat or a temperature of the energy device. The processor causes a notification section to make a notification based on the estimated remaining heat information.

17 Claims, 14 Drawing Sheets

Related U.S. Application Data

(60) Provisional application No. 63/222,252, filed on Jul. 15, 2021, provisional application No. 63/221,128, filed on Jul. 13, 2021.

(51) Int. Cl.

| | |
|---|---|
| *A61B 18/04* | (2006.01) |
| *A61B 18/14* | (2006.01) |
| *G06T 7/00* | (2017.01) |
| *G06T 7/11* | (2017.01) |
| *G06V 10/25* | (2022.01) |
| *G16H 30/40* | (2018.01) |
| *G16H 50/20* | (2018.01) |
| *A61B 17/00* | (2006.01) |
| *A61B 18/00* | (2006.01) |
| *G06V 10/70* | (2022.01) |

(52) U.S. Cl.
CPC .............. *G06T 7/0012* (2013.01); *G06T 7/11* (2017.01); *G06V 10/25* (2022.01); *G16H 30/40* (2018.01); *G16H 50/20* (2018.01); *A61B 2017/0042* (2013.01); *A61B 2018/00577* (2013.01); *A61B 2018/00702* (2013.01); *A61B 2018/00791* (2013.01); *A61B 2018/00898* (2013.01); *G06T 2207/10068* (2013.01); *G06T 2207/20081* (2013.01); *G06T 2207/30024* (2013.01); *G06V 10/70* (2022.01)

(58) Field of Classification Search
CPC  A61B 2018/00791; A61B 2018/00898; A61B 34/20
See application file for complete search history.

(56) References Cited

U.S. PATENT DOCUMENTS

| | | | | |
|---|---|---|---|---|
| 10,786,298 | B2 | 9/2020 | Johnson | |
| 2006/0030844 | A1* | 2/2006 | Knight | A61B 18/1492 606/41 |
| 2008/0082145 | A1* | 4/2008 | Skwarek | A61B 18/1206 607/60 |
| 2009/0024023 | A1* | 1/2009 | Welches | A61B 18/201 600/549 |
| 2013/0245375 | A1 | 9/2013 | DiMaio et al. | |
| 2014/0296842 | A1 | 10/2014 | Mansi et al. | |
| 2015/0272653 | A1* | 10/2015 | Brunke | G16H 50/30 606/27 |
| 2016/0287338 | A1 | 10/2016 | Grady et al. | |
| 2016/0314601 | A1* | 10/2016 | Sankaran | G06T 7/0012 |
| 2017/0079678 | A1* | 3/2017 | Ishikawa | A61B 1/317 |
| 2017/0252095 | A1 | 9/2017 | Johnson | |
| 2018/0160910 | A1 | 6/2018 | Takahashi et al. | |
| 2018/0168734 | A1* | 6/2018 | Strobl | A61B 90/39 |
| 2018/0199987 | A1 | 7/2018 | Sugiyama | |
| 2018/0243031 | A1* | 8/2018 | Markus | A61B 18/24 |
| 2019/0201074 | A1 | 7/2019 | Yates et al. | |
| 2019/0201084 | A1 | 7/2019 | Shelton, IV et al. | |
| 2019/0206565 | A1 | 7/2019 | Shelton, IV | |
| 2019/0262076 | A1 | 8/2019 | Brown | |
| 2019/0298398 | A1 | 10/2019 | Wellman et al. | |
| 2019/0371474 | A1 | 12/2019 | Borsic | |
| 2020/0078081 | A1 | 3/2020 | Jayme et al. | |
| 2020/0188046 | A1 | 6/2020 | Overmyer et al. | |
| 2020/0197072 | A1* | 6/2020 | Watson | A61B 34/74 |
| 2020/0265309 | A1* | 8/2020 | Wham | G06N 3/0464 |
| 2020/0330144 | A1 | 10/2020 | Moriwaki et al. | |
| 2021/0015554 | A1 | 1/2021 | Chow et al. | |
| 2021/0038295 | A1 | 2/2021 | Katsuragi et al. | |
| 2021/0038314 | A1 | 2/2021 | Wibowo | |
| 2021/0085387 | A1 | 3/2021 | Amit et al. | |
| 2021/0161588 | A1 | 6/2021 | Fujisawa et al. | |
| 2021/0196425 | A1 | 7/2021 | Shelton, IV et al. | |
| 2021/0267544 | A1* | 9/2021 | Saikou | A61B 34/10 |
| 2021/0401397 | A1 | 12/2021 | Kruecker et al. | |
| 2022/0104884 | A1 | 4/2022 | Leiderman et al. | |
| 2022/0151721 | A1 | 5/2022 | Haraguchi et al. | |
| 2022/0246307 | A1 | 8/2022 | Nakamura | |
| 2023/0240512 | A1 | 8/2023 | Arai et al. | |
| 2023/0380695 | A1 | 11/2023 | Arai et al. | |
| 2023/0410298 | A1 | 12/2023 | Fujii et al. | |
| 2023/0419486 | A1 | 12/2023 | Nishikawa et al. | |

FOREIGN PATENT DOCUMENTS

| | | |
|---|---|---|
| JP | H11-197159 A | 7/1999 |
| JP | 2018-511403 A | 4/2018 |
| JP | 2019-170809 A | 10/2019 |
| JP | 2020-146374 A | 9/2020 |
| JP | 2021-013722 A | 2/2021 |
| JP | 2021-029258 A | 3/2021 |
| JP | 2021-029979 A | 3/2021 |
| JP | 2021-049341 A | 4/2021 |
| JP | 2021-083969 A | 6/2021 |
| JP | 2021-083970 A | 6/2021 |
| JP | 2021-514724 A | 6/2021 |
| JP | 2021/188883 A | 12/2021 |
| WO | 2016/161293 A1 | 10/2016 |
| WO | 2017/090165 A1 | 6/2017 |
| WO | 2019134009 A1 | 7/2019 |
| WO | 2019/162809 A1 | 8/2019 |
| WO | 2020/031069 A1 | 2/2020 |
| WO | 2020/051444 A1 | 3/2020 |
| WO | 2020/095389 A1 | 5/2020 |
| WO | 2020/104308 A1 | 5/2020 |
| WO | 2021/039298 A1 | 3/2021 |
| WO | 2023/286334 A1 | 1/2023 |

OTHER PUBLICATIONS

K. Naruki, et al., "Proposal for Endoscope Robot with Surgical Scene Recognition using Image Processing", No. 16-2 Proceedings of the 2016 JSME Conference on Robotics and Mechatronics, Yokohama, Japan, Jun. 8-11, 2016, 1A2-02a1(1)-(4), DOI:https://doi.org/10.1299/jsmermd.2016.1A2-02a1.

US Final Office dated Jan. 8, 2026 received in U.S. Appl. No. 18/368,100.

US Office Action dated Sep. 17, 2025 received in U.S. Appl. No. 18/368,100.

US Office Action dated Feb. 17, 2026 received in U.S. Appl. No. 18/118,342.

\* cited by examiner

| ESTIMATION RESULT OF REMAINING HEAT INFORMATION | OPERATION OF NOTIFICATION SECTION |
| --- | --- |
| MORE THAN THRESHOLD | NOTIFY ALERT |
| EQUAL TO OR LESS THAN THRESHOLD | NOT NOTIFY ALERT |

SYSTEM, INFORMATION STORAGE MEDIUM, AND INFORMATION PROCESSING METHOD

CROSS REFERENCE TO RELATED APPLICATIONS

This application is a continuation of International Patent Application No. PCT/JP2022/009694, having an international filing date of Mar. 7, 2022, which designated the United States, the entirety of which is incorporated herein by reference. U.S. Provisional Patent Application No. 63/221, 128 filed on Jul. 13, 2021 and U.S. Provisional Patent Application No. 63/222,252 filed on Jul. 15, 2021 are also incorporated herein by reference in its entirety.

BACKGROUND OF THE INVENTION

The present disclosure relates to a system, a program, and an information processing method or the like.

U.S. Patent Application Publication No. 2018/0160910 discloses a medical device that displays presence or absence of the device in a state of high temperature and a warning message on an endoscope image when there is an energy treatment tool after use in the state of high temperature in the endoscope image. Additionally, the device displays an image indicating a direction of the treatment tool when there is no energy treatment tool in the state of high temperature in the endoscope image.

SUMMARY OF THE INVENTION

In accordance with one of some aspect, there is provided a system comprising:

a memory configured to store a trained model that is trained to output, from a training device tissue image, in which at least one energy device that receives energy supply to output energy and at least one biological tissue are captured, or a training tissue image, in which the at least one biological tissue is captured, and from training information regarding an amount of energy supply, the training information regarding an energy output setting of the energy device, remaining heat information regarding an amount of heat remaining in the energy device or a temperature thereof after energy is supplied to the energy device; and a processor, wherein the processor acquires at least one treatment image including an image in which the at least one energy device and the at least one biological tissue are captured, acquires information regarding an amount of energy supply, the information regarding an energy output setting of the energy device, estimates, based on the treatment image, the information regarding the amount of energy supply, and the trained model, estimated remaining heat information regarding an amount of heat or a temperature of the energy device, and causes a notification section to make a notification based on the estimated remaining heat information.

In accordance with one of some aspect, there is provided a computer-readable non-transitory information storage medium storing a program for causing a computer to execute:

acquiring at least one treatment image including an image in which at least one energy device and at least one biological tissue are captured;

acquiring information regarding an amount of energy supply, the information regarding an energy output setting of the energy device;

estimating, based on a trained model, the treatment image, and the information regarding the amount of energy supply, estimated remaining heat information regarding an amount of heat or a temperature of the energy device, the trained model being trained to output, from a training device tissue image, in which at least one energy device that receives energy supply to output energy and at least one biological tissue are captured, or a training tissue image, in which the at least one biological tissue is captured, remaining heat information regarding an amount of heat remaining in the energy device or a temperature thereof after energy is supplied to the energy device; and displaying the estimated remaining heat information on a monitor.

In accordance with one of some aspect, there is provided an information processing method, comprising:

acquiring at least one treatment image including an image in which at least one energy device and at least one biological tissue are captured;

acquiring information regarding an amount of energy supply, the information regarding an energy output setting of the energy device;

estimating, based on a trained model, the treatment image, and the information regarding the amount of energy supply, estimated remaining heat information regarding an amount of heat or a temperature of the energy device, the trained model being trained to output, from a training device tissue image, in which at least one energy device that receives energy supply to output energy and at least one biological tissue are captured, or a training tissue image, in which the at least one biological tissue is captured, remaining heat information regarding an amount of heat remaining in the energy device or a temperature thereof after energy is supplied to the energy device; and displaying the estimated remaining heat information on a monitor.

DETAILED DESCRIPTION

Figure 1:
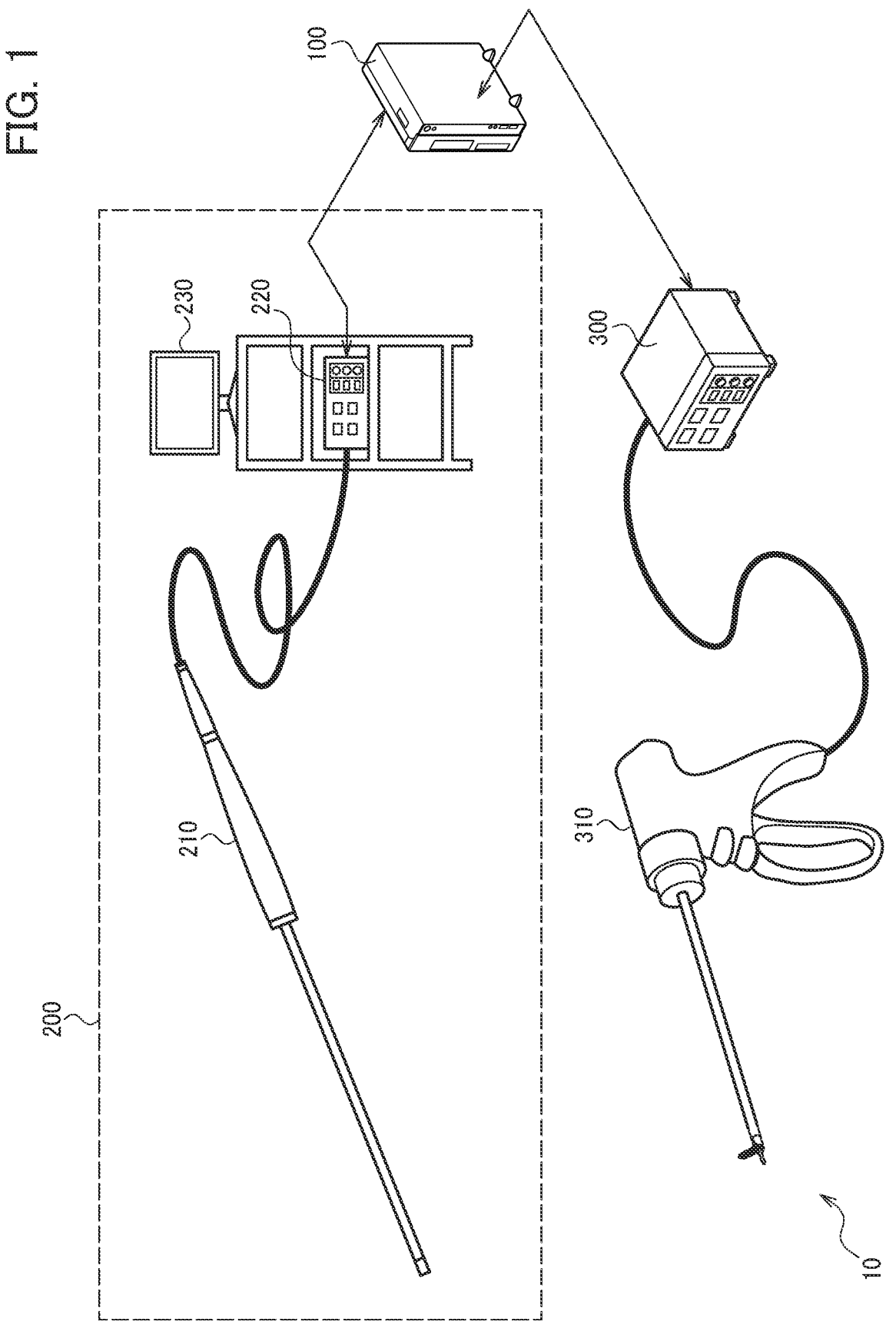
FIG. 1 is a configuration example of a system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. System

FIG. 1 is a configuration example of a system 10 according to the present embodiment. FIG. 1 shows a configuration example of the system for capturing images of a surgical field using an endoscope. The system 10 shown in FIG. 1 includes a controller 100, an endoscope system 200, a generator 300, and an energy device 310. The system 10 is a surgery system for performing surgery using at least one energy device under an endoscope. Although an example in which the system 10 includes a single energy device 310 is shown, the system 10 may include a plurality of energy devices.

The endoscope system 200 is a system that performs imaging by an endoscope, image processing of the endoscope images, and display of the endoscope images in a monitor. The endoscope system 200 includes an endoscope 210, a main body device 220, and a notification section 230. Herein, a rigid mirror for surgical operation is described as an example.

The endoscope 210 includes an insertion section to be inserted into a body cavity, an operation section to be connected to the base end of the insertion section, a universal cord connected to the base end of the operation section, and a connector section to be connected to the base end of the universal cord. The insertion section includes a rigid tube, an objective optical system, an image sensor, an illumination optical system, a transmission cable, and a light guide. The objective optical system and the image sensor for capturing images inside the body cavity and the illumination optical system for illuminating the inside of the body cavity are installed in the distal end section of the rigid tube having an elongated cylindrical shape. The distal end section of the rigid tube may be configured to be bendable. The transmission cable that transmits image signals acquired by the image sensor, and the light guide that guides the illumination light to the illumination optical system are provided inside the rigid tube. The operation section is held by the user and accepts operations from the user. The operation section has buttons to which various functions are assigned. When the distal end of the insertion section is bendable, an angle operation lever is provided in the operation section. The connector section includes a video connector that detachably connects the transmission cable to the main body device 220, and a light guide connector that detachably connects the light guide to the main body device 220.

The main body device 220 includes a processing device that controls the endoscope, performs image processing of endoscope images, and displays the endoscope images, and a light source device that generates and controls illumination light. The main body device 220 is also called a video system center. The processing device is constituted of a processor such as a CPU, and performs image processing of the image signals transmitted from the endoscope 210 to generate endoscope images and then outputs the endoscope images to the notification section 230 and the controller 100. The illumination light emitted from the light source device is guided by the light guide to the illumination optical system and is emitted from the illumination optical system into the body cavity.

The energy device 310 is a device that outputs energy by high-frequency power, ultrasonic waves, or the like from its distal end section to perform treatments including coagulation, sealing, hemostasis, incision, division, dissection, or the like, with respect to tissues in contact with its distal end section. The energy device 310 is also referred to as an energy treatment tool. The energy device 310 may be a monopolar device in which high-frequency power is energized between an electrode at the distal end of the device and an electrode outside the body, a bipolar device in which high-frequency power is energized between two jaws, an ultrasonic device which has a probe and a jaw and emits ultrasonic waves from the probe, a combination device in which high-frequency power is energized between the probe and the jaw and also emits ultrasonic waves from the probe, or the like.

The generator 300 supplies energy to the energy device 310, controls the energy supply, and acquires electrical information from the energy device 310. When the energy device 310 outputs high-frequency energy, the generator 300 provides high-frequency power, and the energy device 310 outputs the high-frequency power from the electrode or jaw. When the energy device 310 outputs ultrasonic energy, the generator 300 provides electric power, and the probe of the energy device 310 converts the electric power into ultrasonic waves and outputs the ultrasonic waves.

The electrical information refers to electrical information of the tissue that comes in contact with the electrode or jaw of the energy device 310; more specifically, the electrical information is information obtained as a response to the output of the high-frequency power to the tissue by the energy device 310. The electrical information is, for example, impedance information of the tissue to be treated by the energy device 310. However, as described later, the electrical information is not limited to impedance information.

The generator 300 performs control of time-based change in the energy output from the energy device 310 according to an output sequence. The generator 300 may vary the energy output according to the time-based change in the impedance information. In this case, the output sequence may specify how the energy output is changed in response to the change in the impedance information. The generator 300 may also automatically turn off the energy output according to the time-based change in the impedance information. For example, the generator 300 may determine that the treatment is completed when the impedance rises to a certain level or higher, and may turn off the energy output.

The controller 100 acquires images and energy information from the endoscope system 200 and the generator 300. Then, the controller 100 estimates a remaining heat and outputs the estimation result to the monitor to notify a surgeon.

Information regarding a biological tissue includes information regarding not only a specific organ but also a portion accompanying an organ, such as a tissue connecting between organs. The energy device 310 is a monopolar device 320, a bipolar device 330, an ultrasonic device 340 or the like as described in FIGS. 4-6 below, but may be a device other than these devices.

The generator 300 adjusts the energy output of the energy device 310 according to an energy output adjustment instruction. Specifically, the system 10 of the present embodiment is a system that automatically adjusts the energy output from the energy device 310 based on endoscope images. The generator 300 supplies energy to the energy device 310 in the amount of energy supply directed by the energy output adjustment instruction. As the energy device 310 receives the energy supply and performs energy output accordingly, the energy output is adjusted according to the energy output adjustment instruction.

The energy output adjustment instruction includes an instruction to increase or decrease the output as the overall waveform of the output sequence, an instruction to set an output sequence from among a plurality of selectable output sequences, and the like. For example, when the energy output from the energy device 310 is adjustable by a staged magnification factor, the energy output adjustment instruction is an instruction indicating the staged magnification factor for the energy output. The generator 300 increases or decreases the high-frequency output or ultrasound output according to the magnification factor thus instructed. The magnification factor may be continuously adjustable. In another case where a plurality of output sequences is provided, the energy output adjustment instruction is an instruction to specify one of these plural output sequences. The generator 300 performs energy output from the energy device 310 according to the output sequence thus instructed. The energy output adjustment instruction may include both of the instruction to increase or decrease the energy output, and an instruction to change the output sequence.

2. Controller

Figure 2:
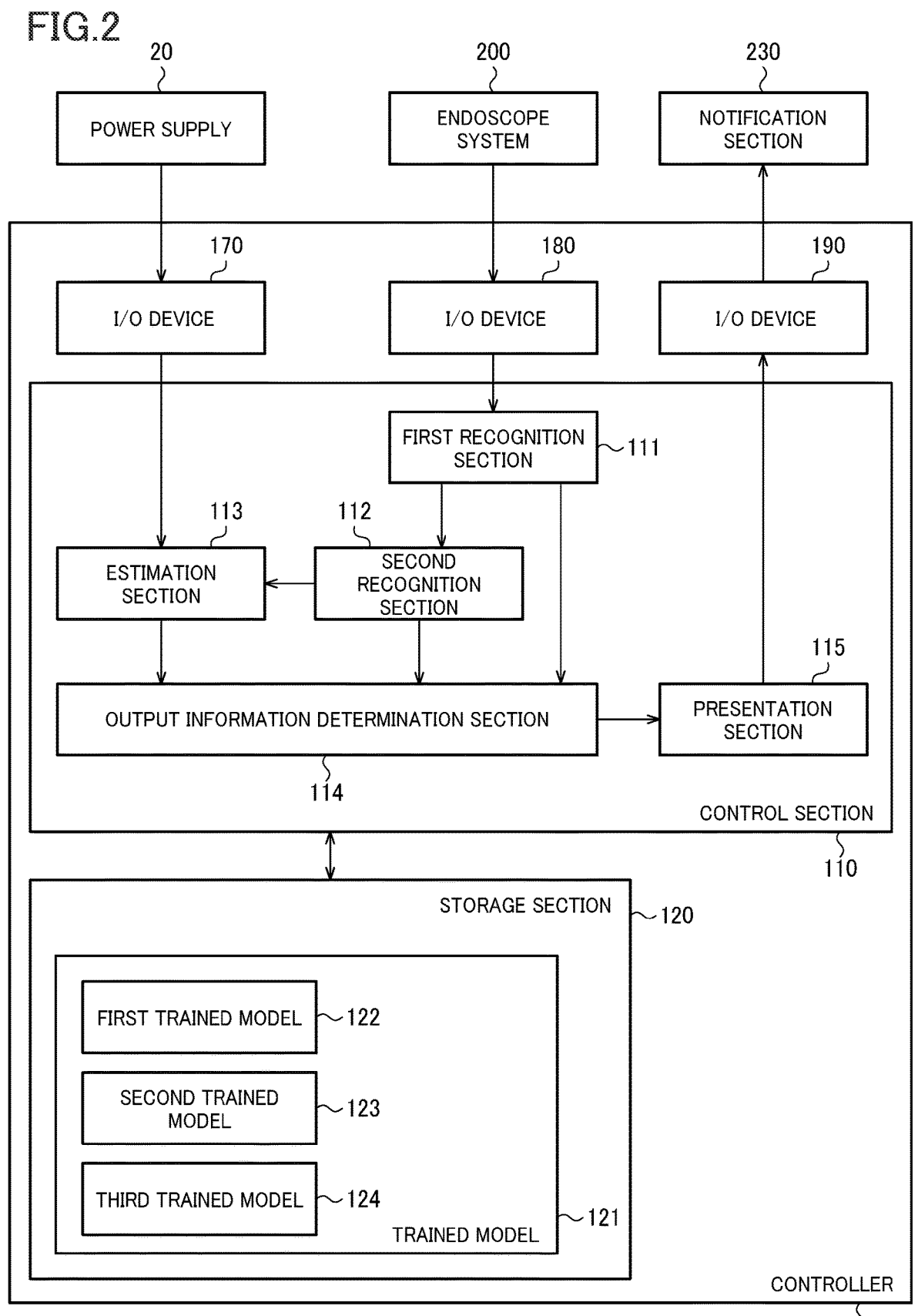
FIG. 2 is a configuration example of a controller.

FIG. 2 is a configuration example of the controller 100. The controller 100 controls the overall system 10. The controller 100 includes a control section 110, a storage section 120, and I/O devices 170, 180, and 190. FIGS. 1 and 2 show an example in which the controller 100 is constituted of a device separated from the generator 300. In this case, the controller 100 is constituted of an information processing device, such as a PC, a server device, or the like. Alternatively, the controller 100 may be implemented by a cloud system that performs the processes with one or a plurality of information processing devices connected via a network.

The I/O device 180 receives image data of an endoscope image from the main body device 220 of the endoscope system 200. The I/O device 180 is a connector to which an image transmission cable is connected, or an interface circuit connected to the connector to perform communication with the main body device 220.

The I/O device 190 is an interface circuit used for output to the notification section 230. The I/O device 190 is a connector to which a signal transmission cable is connected, or is connected to the connector to perform communication with the notification section 230. In addition, the I/O device 170 is an interface circuit used for power supply.

The control section 110 estimates, from an endoscope image, estimated remaining heat information regarding an amount of heat or a temperature of the energy device 310 by image recognition process using a trained model 121, and causes the notification section 230 to make a notification based on the information. The control section 110 includes one or a plurality of processors serving as hardware. The processor is a general-purpose processor such as a CPU (Central Processing Unit), a GPU (Graphical Processing Unit), a DSP (Digital Signal Processor), or the like. Alternatively, the processor may be a dedicated processor such as an ASIC (Application Specific Integrated Circuit), an FPGA (Field Programmable Gate Array), or the like.

The storage section 120 stores the trained model 121 used for the image recognition process. For example, when the image recognition process is performed by a general-purpose processor, the storage section 120 stores, as the trained model 121, a program that describes an inference algorithm and parameters used for the inference algorithm. The trained model 121 includes a first trained model 122, a second trained model 123, and a third trained model 124. The first trained model 122 is the trained model 121 associated with estimation of a biological tissue as described in FIG. 14 below. In addition, the second trained model 123 is the trained model 121 associated with estimation of the energy device 310, and the third trained model 124 is the trained model 121 associated with estimation of a remaining heat. When the image recognition process is performed by a dedicated processor with a hardware inference algorithm, the storage section 120 stores the parameters used for the inference algorithm as the trained model 121. The storage section 120 is a storage device, such as a semiconductor memory, a hard disk drive, an optical disc drive, or the like. The semiconductor memory is, for example, a RAM, a ROM, a nonvolatile memory or the like.

For example, a neural network may be used as the inference algorithm of the image recognition process. Weight coefficients and a bias of the inter-node connections in the neural network correspond to the parameters. The neural network includes an input layer to which image data is entered, an intermediate layer for performing a calculation process with respect to the data input via the input layer, and an output layer for outputting recognition results based on the calculation result output from the intermediate layer. For example, a CNN (Convolutional Neural Network) may be used as the neural network to be used for the image recognition process.

The control section 110 also includes a first recognition section 111, a second recognition section 112, an estimation section 113, an output information determination section 114, and a presentation section 115. The storage section 120 stores programs describing the functions of the first recognition section 111, the second recognition section 112, the estimation section 113, the output information determination section 114, and the presentation section 115. One or more processors in the control section 110 read out the programs from the storage section 120 and executes the programs, thereby implementing the functions of the first recognition section 111, the second recognition section 112, the estimation section 113, the output information determination section 114, and the presentation section 115. The programs describing the functions of each of these sections may be stored in a non-transitory information storage medium, which is a computer-readable medium. The information storage medium can be implemented by, for example, an optical disc, a memory card, an HDD, a semiconductor memory, or the like. The semiconductor memory is, for example, a ROM or a nonvolatile memory.

Figure 3:
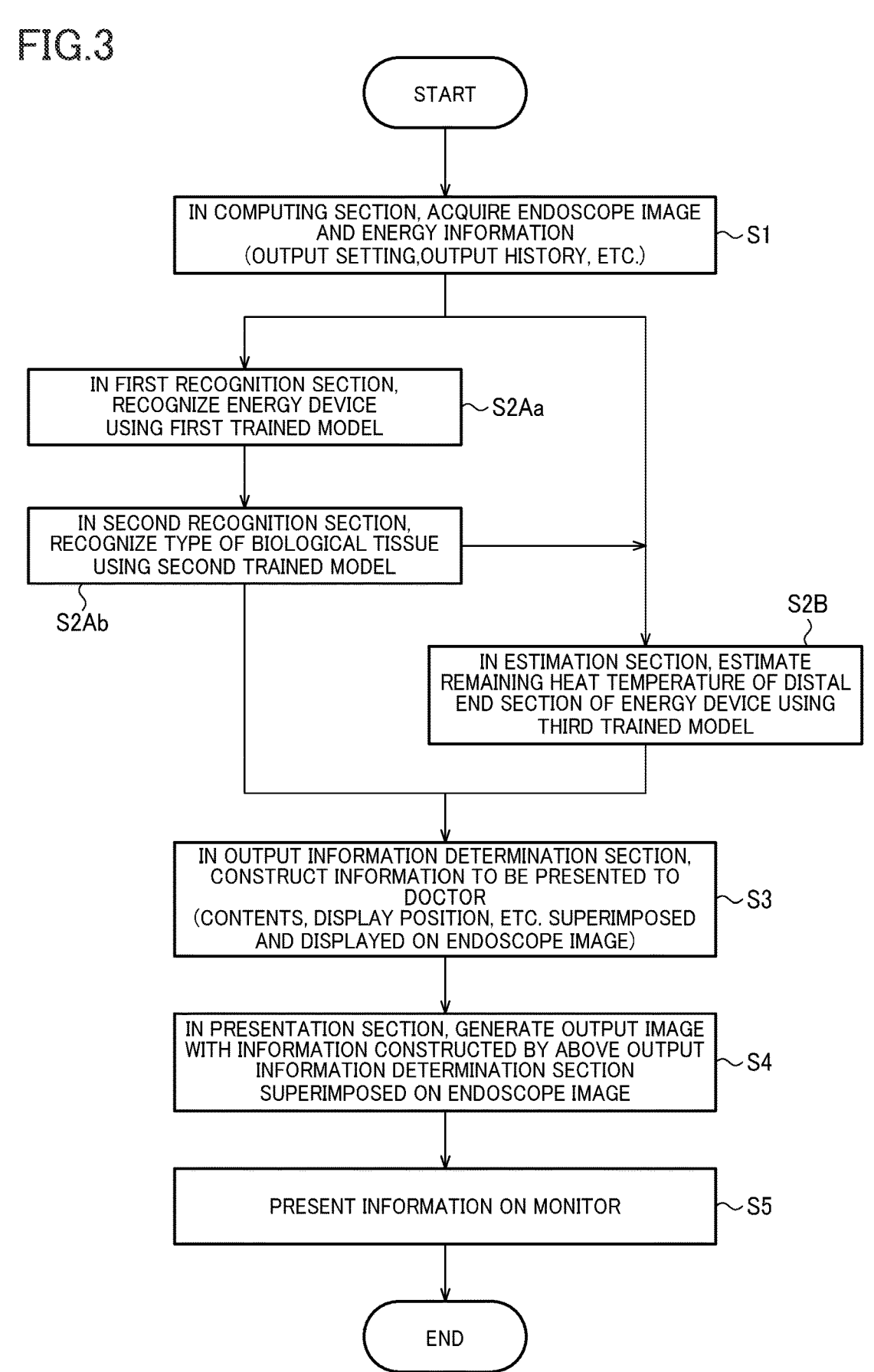
FIG. 3 is a flowchart for explaining processing performed by a system.

FIG. 3 is a flowchart for explaining processing when the controller 100 analyzes remaining heat information of the energy device 310 and presents the information to a doctor. First, in the step S1, the control section 110 acquires an endoscope image and the energy information from the main body device 220 of the endoscope system 200 via the I/O device 180. The endoscope image is, for example, an image in which the energy device 310 or a biological tissue, or both of them is captured, also referred to as a process image. In addition, the energy information refers to, for example, information regarding an energy output setting, output history, or the like.

Figure 5:
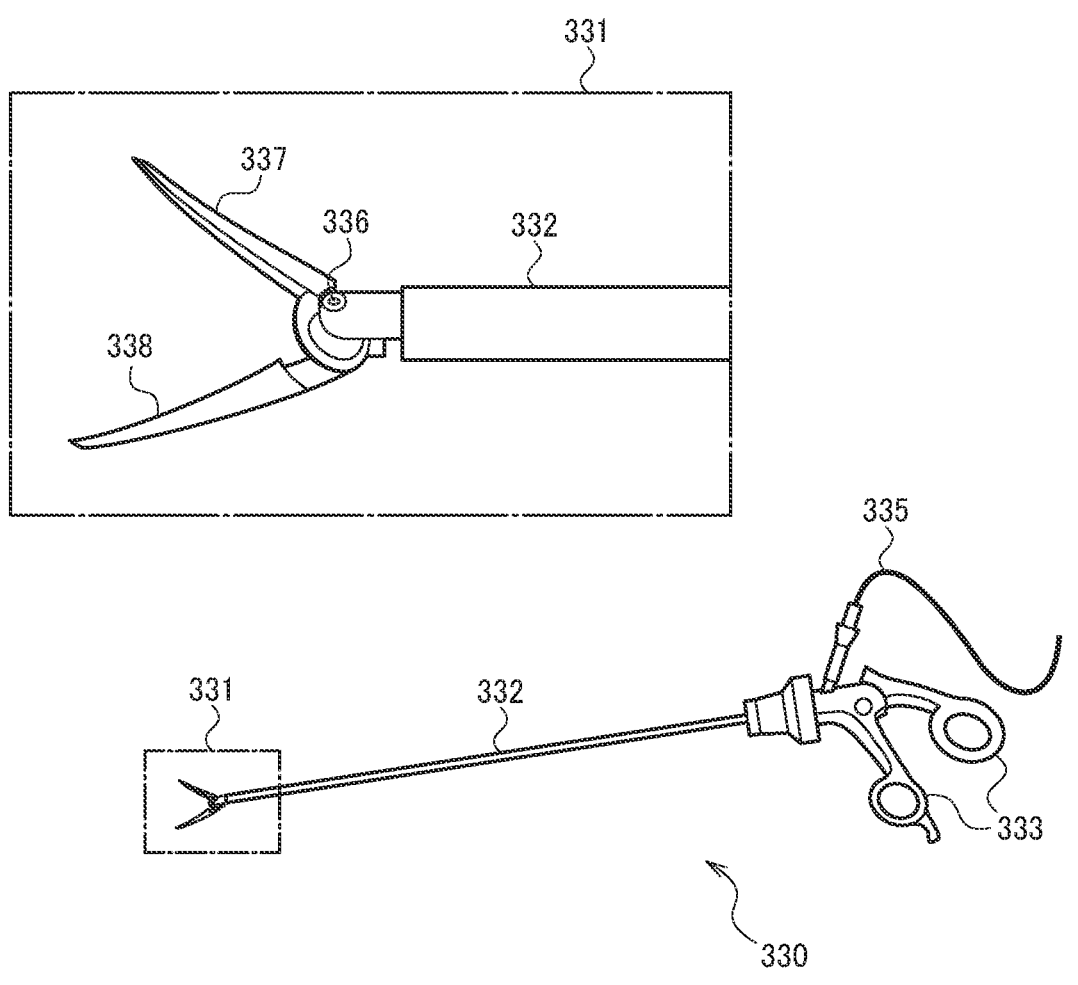
FIG. 5 is a configuration example of a bipolar device.
Figure 12:
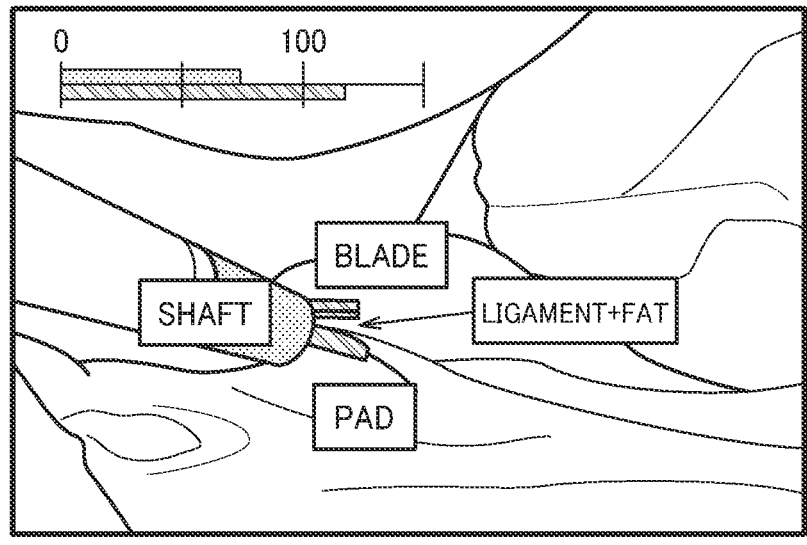
FIG. 12 is a display example of remaining heat information.

Next, the control section 110 performs the steps S2Aa, S2Ab, and S2B. In the step S2Aa, the first recognition section 111 performs the image recognition process using the first trained model 122 with respect to the endoscope image, thereby estimating the energy device 310 based on the image. In the step S2Ab, the second recognition section 112 performs the image recognition process using the second trained model 123 with respect to the endoscope image, thereby estimating a biological tissue based on the image. On the other hand, in the step S2B, the estimation section 113 performs the image recognition process using the third trained model 124 with respect to the endoscope image, thereby estimating the remaining heat temperature of the distal end section of the energy device 310. The distal end section refers to a section around a site to which the energy from the energy device 310 is output. For example, when the energy device 310 is the bipolar device 330 as illustrated in FIG. 5 below, the distal end section refers to a blade, a pad, and a shaft as illustrated in FIG. 12 below. Note that the information regarding the energy device 310 estimated in the step S2Aa and the information regarding the biological tissue estimated in the step S2Ab are information that affects the remaining heat information of the energy device 310, heat diffusion to the biological tissue, or the like.

Next, in the step S3, the output information determination section 114 constructs information to be presented to the doctor based on the estimation results of the steps S2Aa and S2B. For example, it constructs information regarding display indicating the energy device 310, the biological tissue, a temperature, or the like and a display position thereof.

Next, in the step S4, the presentation section 115 generates an image to be displayed on the notification section based on the information regarding the contents such as the display position or the like constructed by the output information determination section 114. For example, it generates one image by superimposing a temperature zone or the like to be displayed on the endoscope image. Then, in the step S5, the notification section 230 displays the image generated by the presentation section 115 according to an instruction from the control section 110.

3. Energy Device

In the following, a monopolar device 320, a bipolar device 330, an ultrasonic device 340, and a combination device are described as examples of the energy device 310.

Figure 4:
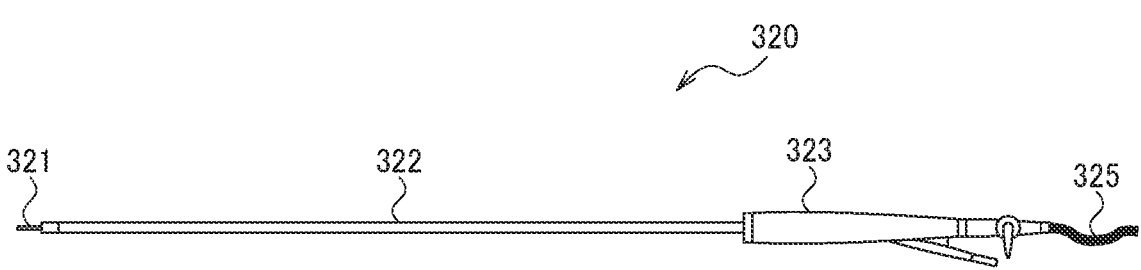
FIG. 4 is a configuration example of a monopolar device.

FIG. 4 is a configuration example of the monopolar device 320. The monopolar device 320 includes an insertion section 322 having an elongated cylindrical shape, an electrode 321 provided at the distal end of the insertion section 322, an operation section 323 connected to the base end of the insertion section 322, and a cable 325 connecting the operation section 323 and a connector (not shown). The connector is detachably connected to the generator 300.

The high-frequency power output by the generator 300 is transmitted by the cable 325 and output from the electrode 321. A counter electrode plate is provided outside a patient's body, and energization occurs between the electrode 321 and the counter electrode plate. This applies high-frequency energy to a tissue in contact with the electrode 321, and Joule heat is generated in the tissue. Electrodes having various shapes are used for the electrode 321 depending on the type of the treatment. The monopolar device 320 is capable of adjusting the degree of coagulation and incision by changing the energization pattern.

FIG. 5 is a configuration example of the bipolar device 330. The bipolar device 330 includes an insertion section 332 having an elongated cylindrical shape, two jaws 337 and 338 provided at the distal end section 331 of the insertion section 332, an operation section 333 connected to the base end of the insertion section 332, and a cable 335 connecting the operation section 333 and a connector (not shown). The connector is detachably connected to the generator 300. The jaws 337 and 338 are movable portions for gripping a tissue and also applying energy to the gripped tissue. The jaws 337 and 338 are structured to be openable/closable around an axis provided at the base end 336. The operation section 333 has a grip section for operating the opening and closing of the jaws 337 and 338. When a doctor tightly holds the grip section, the jaws 337 and 338 are closed to grip the tissue.

The high-frequency power output by the generator 300 is transmitted by the cable 335, and, when the jaws 337 and 338 grip a tissue, energization occurs between the two jaws 337 and 338. As a result, high-frequency energy is applied to the tissue sandwiched between the two jaws 337 and 338, Joule heat is generated in the tissue, and the tissue is coagulated. The generator 300 may measure the impedance information of the tissue gripped by the jaws 337 and 338, detect completion of the treatment based on the impedance information, and may automatically stop the energy output. Further, the generator 300 may also automatically adjust the energy applied to the tissue based on the impedance information. For example, the device temperature of the bipolar device 330 rises to about 100 degrees Celsius.

A vessel sealing device is a derivative device of the bipolar device. The vessel sealing device is a bipolar device provided with a cutter on its jaw, and separates a tissue by running the cutter after coagulating the tissue by energization.

Figure 6:
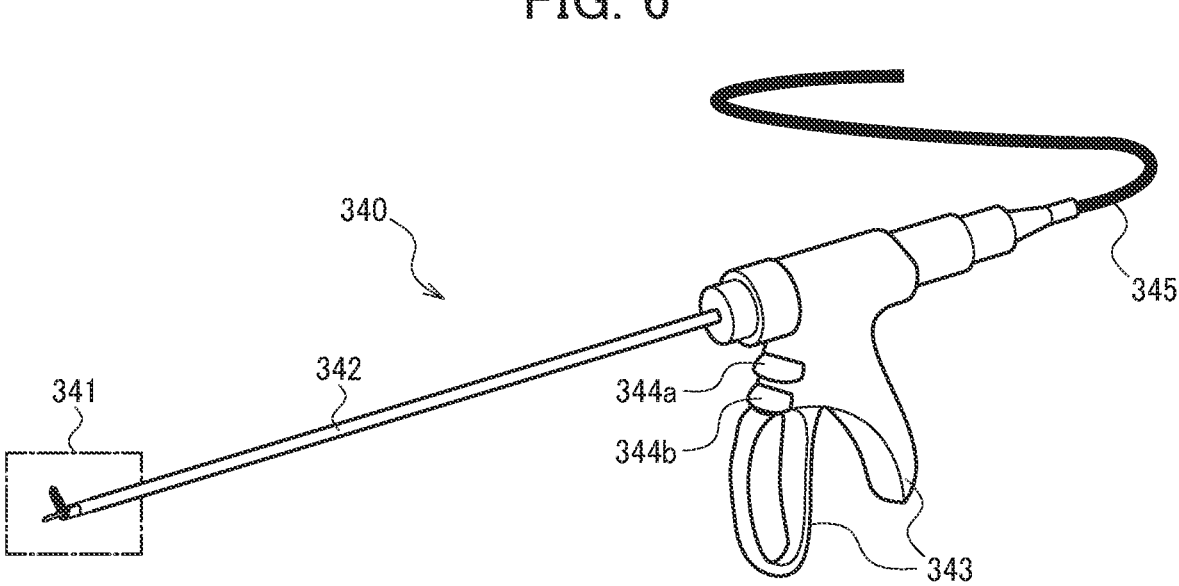
FIG. 6 is a configuration example of an ultrasonic device.
Figure 6:
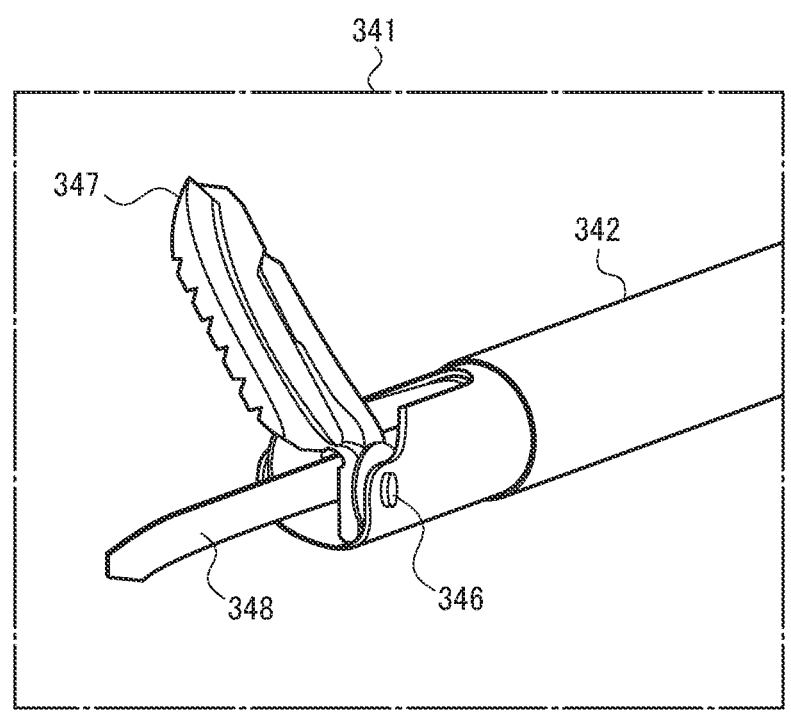

FIG. 6 is a configuration example of the ultrasonic device 340. The ultrasonic device 340 includes an insertion section 342 having an elongated cylindrical shape, a jaw 347 and a probe 348 provided at a distal end section 341 of the insertion section 342, an operation section 343 connected to the base end of the insertion section 342, and a cable 345 connecting the operation section 343 and a connector (not shown). The connector is detachably connected to the generator 300. The jaw 347 is movable around an axis provided at the base end 346, and is structured to be openable/closable with respect to the non-movable probe 348. The operation section 343 has a grip section for operating the opening and closing of the jaw 347. When a doctor tightly holds the grip section, the jaw 347 is closed, and the jaw 347 and the probe 348 grip a tissue. The operation section 343 is provided with an operation button 344a to which a first output mode is assigned, and an operation button 344b to which a second output mode is assigned. The output mode is selected according to what treatment is to be performed. When the operation button for each output mode is pressed, ultrasonic energy is output in the output sequence for the corresponding mode.

The power output by the generator 300 is transmitted by the cable 335, and when the operation button 344a or the operation button 344b is pressed, the probe 348 converts the power into ultrasonic waves and outputs the ultrasonic waves. As a result, a frictional heat is generated in the tissue sandwiched between the jaw 347 and the probe 348, and the tissue is coagulated or incised. With regard to the heat diffusion of the ultrasonic device, for example, although the heat diffusion of the ultrasonic device 340 is smaller than that of the high-frequency device, the device temperature of the ultrasonic device 340 can rise to nearly 200 degrees Celsius.

The combination device that uses both high-frequency power and ultrasonic waves has a configuration similar to that of the ultrasonic device shown in FIG. 6, for example. However, the combination device is capable of energizing high-frequency power between the jaw and the probe to generate Joule heat in a tissue gripped by the jaw and the probe, thus coagulating the tissue. Similarly to the ultrasonic device, the combination device is also capable of incising a tissue gripped by the jaw and the probe by outputting ultrasonic waves from the probe. A high-frequency mode is assigned to one of the two operation buttons provided on the operation section, and a seal-and-cut mode is assigned to the other one of the two operation buttons. The high-frequency mode is a mode in which coagulation and other treatments are performed using only high-frequency energy output. The seal-and-cut mode is a mode in which high-frequency energy and ultrasonic energy are used in combination, and the tissue is coagulated and separated by high-frequency energy output.

In the following embodiment, an exemplary case where the bipolar device 330 is mainly used as the energy device 310 is described. However, it should be noted that the present embodiment is applicable to any cases of using various energy devices mentioned above that may cause heat diffusion.

4. First Embodiment

Figure 7:
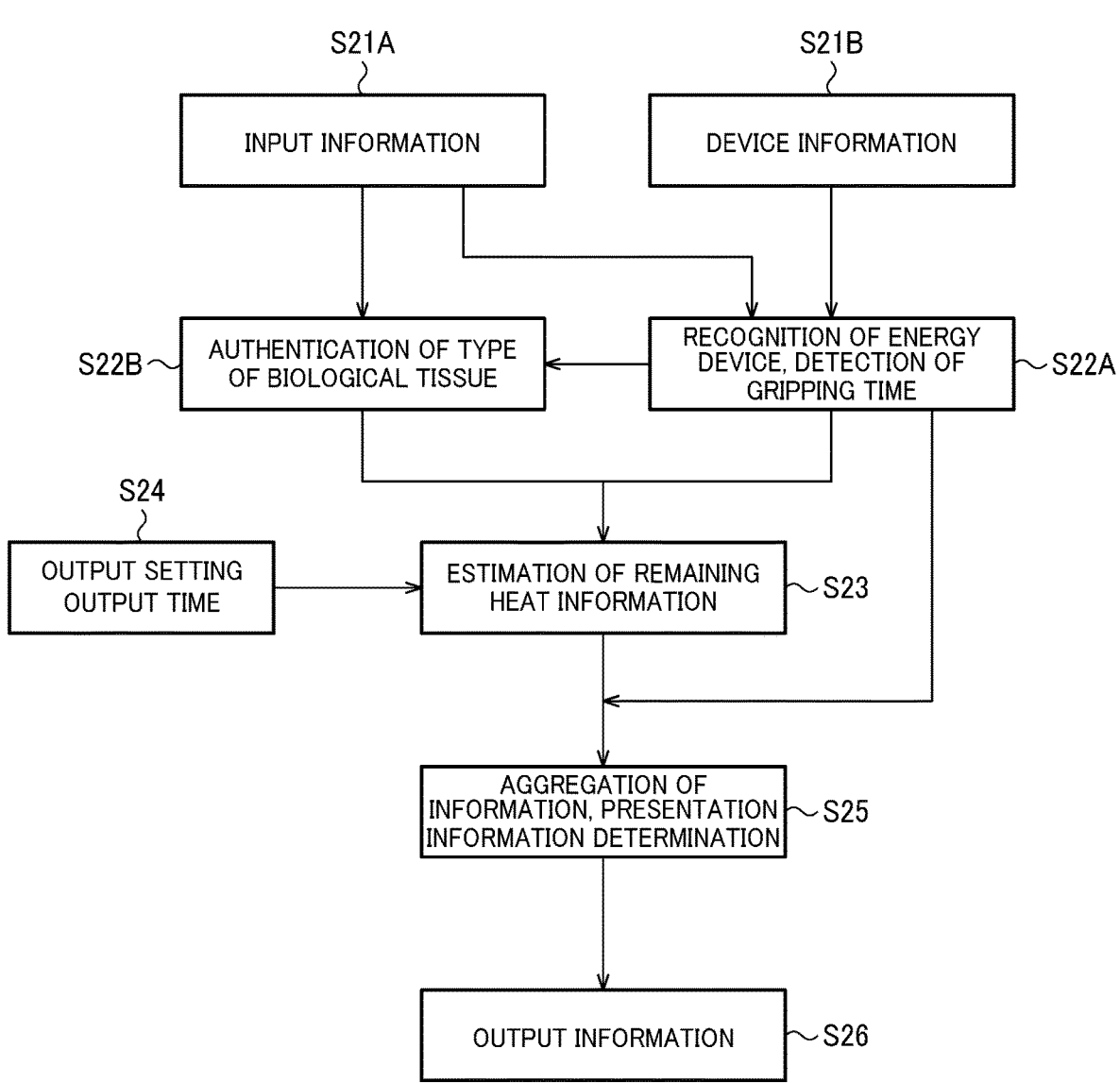
FIG. 7 is an example of processing according to a first embodiment.
Figure 8:
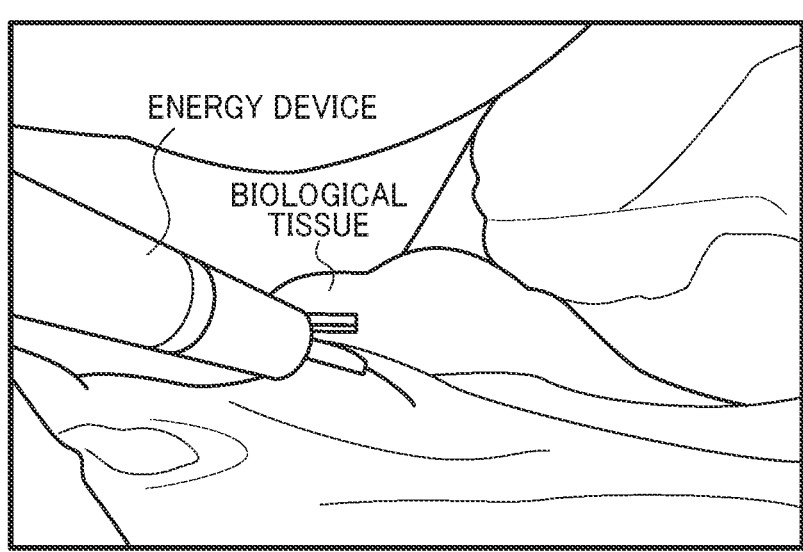
FIG. 8 is an example of a treatment image.

FIG. 7 is an example of processing according to the first embodiment. First, as shown in S21A, an endoscope image is input to the control section 110 by processing of the control section 110. Specifically, each frame image of a moving image captured by the endoscope is sequentially input to the control section 110. In the endoscope image, one or a plurality of energy devices 310 and one or a plurality of biological tissues are captured. Note that in the following description, the endoscope image is referred to as a treatment image as appropriate. FIG. 8 is an example of a treatment image, which corresponds to the input information of S21A in FIG. 7. In this manner, the treatment image to be input to the first recognition section 111 and the second recognition section 112 captures the energy device 310 and the biological tissue.

Next, in S22A, the first recognition section 111 of the control section 110 detects the energy device 310 from the treatment image by executing an estimation program adjusted by machine learning as described in FIG. 14 below. The estimation program is a program for executing the trained model 121 that is trained by a relationship between an amount of heat storage according to energy output information, an amount of heat dissipation according to a tissue type, tissue gripping time by the treatment tool, and the like, as described in FIGS. 14-16 below. In S22A, the first recognition section 111 detects the energy device 310 as the control section 110 inputs the treatment image to a network having the estimation program. Specifically, in S21B, the first recognition section 111 extracts device information from the treatment image. The device information herein is indicative of a type, an existence area, or a condition of the distal end section or the like of the energy device 310. The condition of the distal end section is, for example, an open/close state of the jaws 337 and 338. Note that the input of the device type may be manual input by a doctor. In addition, the treatment image and the device type acquired from the generator 300 or the like are input to the estimation program of the present function to detect the energy device 310 in the treatment image.

Then, the control section 110 estimates, based on the estimation program, a region indicating the energy device 310 among the subjects captured in the treatment image, and labels the region by coloring. In this manner, in S21B, the first recognition section 111 of the control section 110 extracts, from the treatment image, the device information regarding the energy device 310. In addition, in S22A, it detects time during which the energy device 310 grips the biological tissue. Then, the control section 110 outputs the labeled treatment image and the gripping time to the second recognition section 112.

Then, as shown in S22B in FIG. 7, the second recognition section 112 of the control section 110 detects the type of the biological tissue from the treatment image by executing the estimation program as described above. The type of the biological tissue to be detected herein refers to a biological tissue which is a treatment target of the surgery regardless of whether or not it is gripped by the energy device 310. In addition to the biological tissue, it can also detect a gripping amount or gripping time thereof. In this case, the gripping time refers to time elapsed after the tissue is gripped, and can be recognized from the treatment image. For example, the type of the biological tissue includes, but not limited to, a great vessel, a pancreas, a duodenum, or the like. The control section 110 inputs the treatment image labeled in the first recognition section 111 to the network having the estimation program trained by annotating the type of the biological tissue, thereby detecting the type of the biological tissue captured in the treatment image. Note that input of the type of the biological tissue may be manual input by a doctor. In addition to the type of the biological tissue, it can also detect a condition of the biological tissue, such as wet, dry, or the like. Then, labeling of the type of the estimated biological tissue is performed. For example, it is performed by coloring a region of a given biological tissue. In this manner, the second recognition section 112 extracts, from the treatment image, tissue information regarding the biological tissue. Note that, in the above, the biological tissue can also be detected by 3D matching with CT (Computed Tomography) or MRI (Magnetic Resonance Imaging), rather than the endoscope image.

Next, as shown in S23 in FIG. 7, the estimation section 113 of the control section 110 receives the estimation results of the first recognition section 111 and the second recognition section 112 to estimate the remaining heat information based on the estimation results. Here, the estimation section 113 can also perform the above estimation using information regarding the amount of energy supply, in addition to the estimation results of the first recognition section 111 and the second recognition section 112, as shown in S24. The information regarding the amount of energy supply refers to information regarding mainly the energy output setting of the energy device, for example, indicative of an output amount or output time of energy, and can be obtained from the energy device 310. Further, the information regarding the amount of energy supply can also be obtained from the generator 300 or the like. In other words, the estimation section 113 inputs the device information, the tissue information, and the information regarding the amount of energy supply (if available) to the estimation program as described in FIG. 13 below, thereby estimating the remaining heat information of the energy device 310. The remaining heat information is information regarding, for example, the temperature, amount of heat, or the like of the distal end section of the energy device 310. Further, the remaining heat information estimated by the estimation section 113 is referred to as estimated remaining heat information. In this manner, the estimation section 113 of the control section 110 estimates the estimated remaining heat information. To estimate the estimated remaining heat information, for example, the estimation section 113 estimates, from the tissue information and the device information, a treatment target tissue to be treated by the energy device 310. Then, the estimation section 113 can also obtain, from the estimated treatment target tissue, information regarding a tissue around the energy device 310, and estimates, based thereon, heat capacity of a heat transfer pass. Based on the heat capacity of the heat transfer pass, the estimation section 113 can estimate the estimated remaining heat information regarding the energy device 310. In addition, the estimation section 113 may estimate the estimated remaining heat information not only after energy supply but also during energy supply. For example, the estimation section 113 can estimate, based on the device information and the tissue information, the treatment target tissue to be treated by the energy device 310. Then, the heat capacity of the heat transfer pass can be estimated from the estimated treatment target tissue, and based thereon, the remaining heat information of the distal end section of the energy device 310 can be estimated.

In S25 in FIG. 7, the output information determination section 114 determines output information based on the respective output results in S22A, S22B, and S23 above. Specifically, the output information determination section 114 aggregates the information estimated by the first recognition section 111, the second recognition section 112, and the estimation section 113 to determine the information to be presented to a doctor.

Then, in S26 in FIG. 7, the presentation section 115 of the control section 110 causes the notification section 230 to make a notification based on the estimated remaining heat information, which is the information estimated by the estimation section 113 in S25. The method of notification includes displaying an icon on the notification section 230, or notifying by sound or vibration, or the like. Note that the controller 100 may include a function for outputting the energy output adjustment instruction to the generator 300. For example, it may output the energy output adjustment instruction to the generator 300 in accordance with input by a surgeon through an interface which enables input by the surgeon. Alternatively, it may recognize the biological tissue and the energy device 310 from the endoscope image by the image recognition process using machine learning or the like as described above, and based on the recognized information, output the energy output adjustment instruction to the generator 300.

Figure 9:
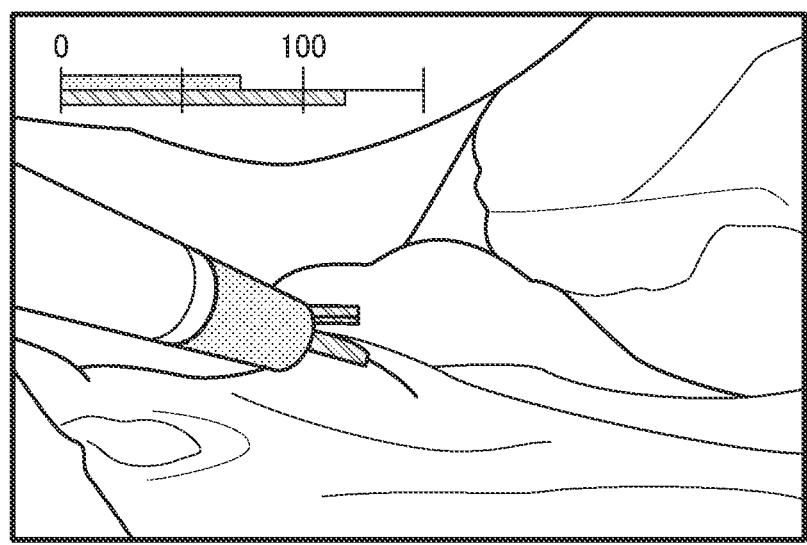
FIG. 9 is a display example of remaining heat information.
Figure 10:
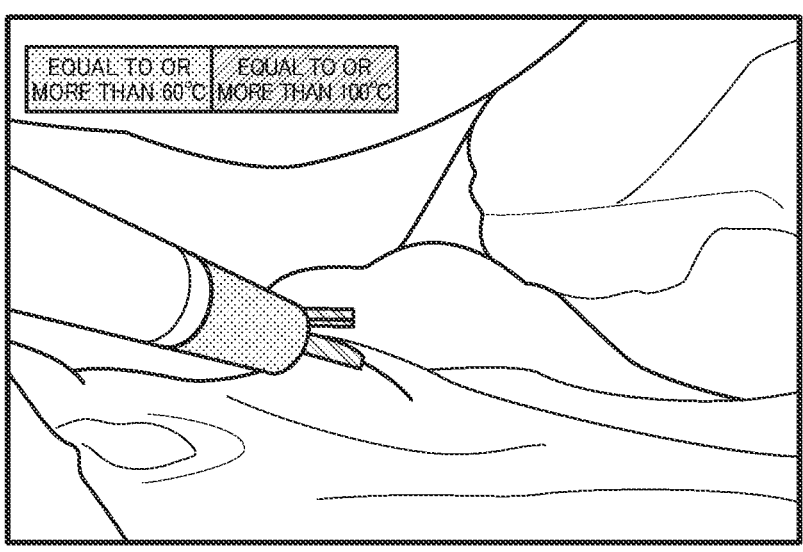
FIG. 10 is a display example of remaining heat information.
Figure 11:
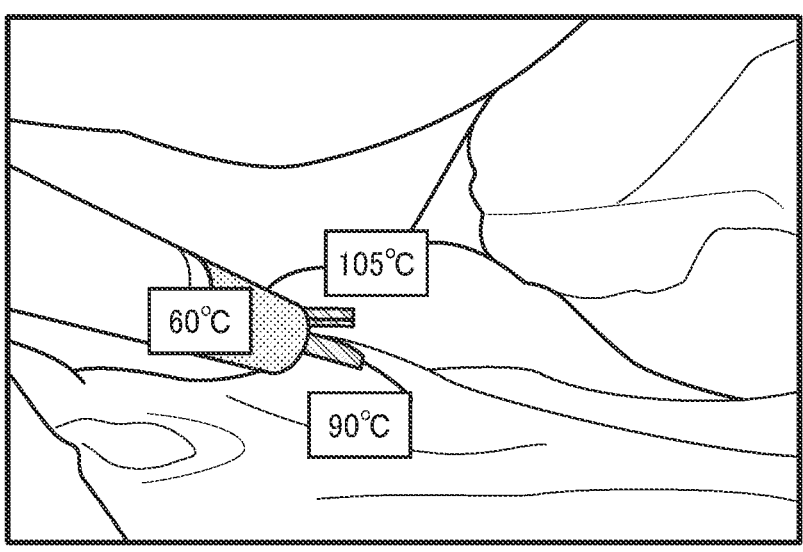
FIG. 11 is a display example of remaining heat information.

FIGS. 9-12 are examples of superimposed images displayed by the presentation section. In the images shown in FIGS. 9-12, a current remaining heat temperature in each site of the distal end section of the energy device 310 is displayed by color. Further, the image shown in FIG. 9 is an example in which a relationship between color and temperature is shown by a bar graph in the upper left of the image. The image shown in FIG. 10 is an example in which the relationship between color and temperature is shown by numerical values in the upper left of the image. The image shown in FIG. 11 shows temperatures by numerical values directly on sites of the distal end section of the energy device 310 so that the relationship between color and temperature can be recognized. In addition, the sites of the distal end section of the energy device 310 may be displayed in the image such that a shaft, a blade, and a pad can be recognized, as in the image shown in FIG. 12. For example, when the blade portion becomes 200 degrees Celsius, the shaft portion, which is connected by metal, may also become hot to about 100 degrees Celsius. However, attention is often not paid to the shaft portion, resulting in a high risk of thermal injury. Therefore, as shown in FIGS. 9-12, displaying the temperature in each site of the distal end section of the energy device 310 will increase effectiveness of risk evaluation of thermal injury. In this manner, the current remaining heat temperature in each site can be displayed by, for example, a bar graph or numerical values. The temperature condition in each site can then be identified, for example, by coloring. The color superimposed display may cause problems with the poor visibility of the distal end section of the energy device 310. In such cases, display settings may be made changeable so that the doctor can choose not to perform the color superimposed display. For example, it may be set not to superimpose color on the blade and pad portions of the distal end section of the energy device 310 in FIG. 12.

Figure 13:
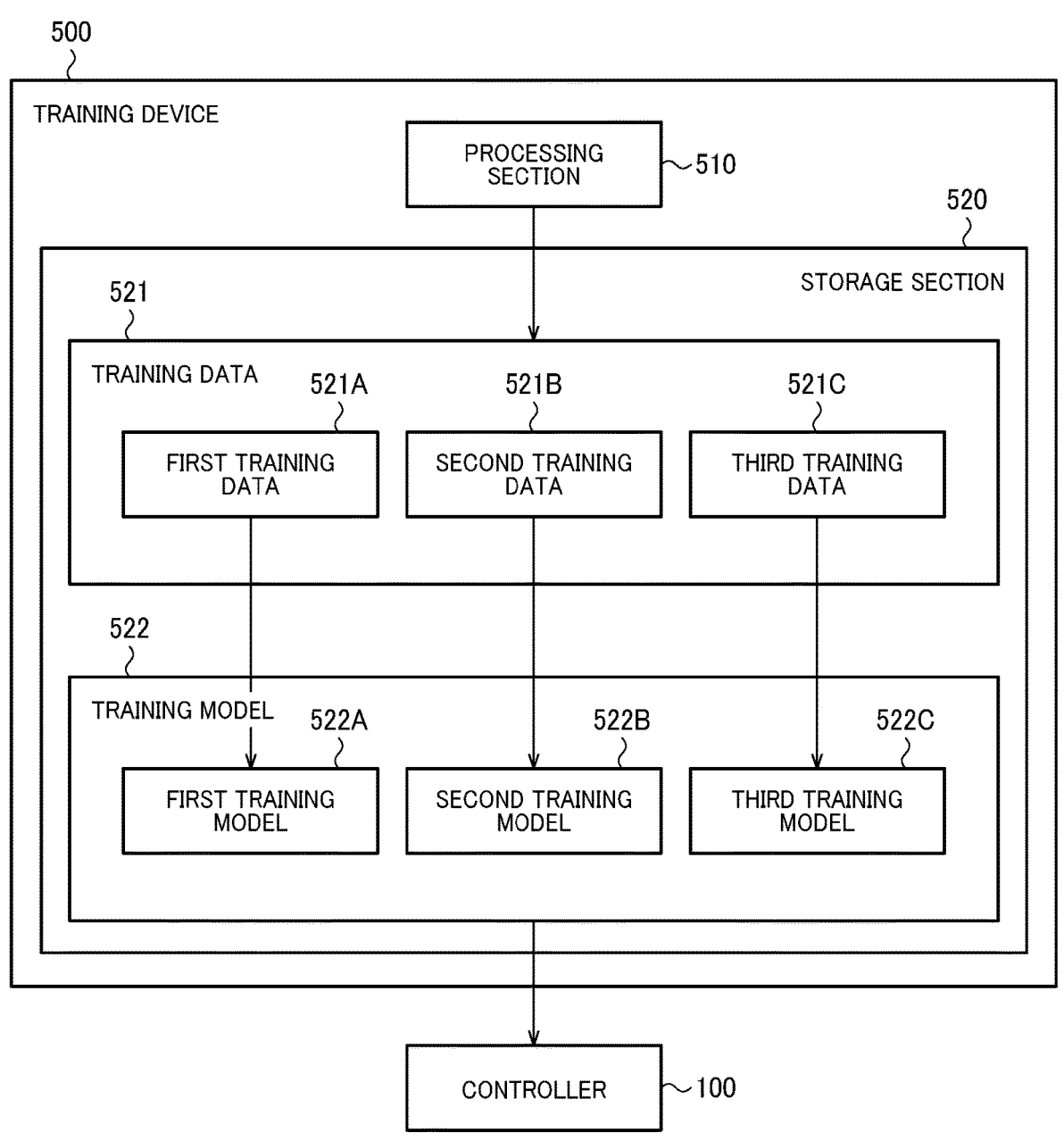
FIG. 13 is a configuration example of a training device.

FIG. 13 is a configuration example of a training device 500 that performs machine learning of the estimation processes of the energy device 310 and the biological tissue as well as the remaining heat information. The training device 500 includes a processing section 510 and a storage section 520. The training device 500 is implemented by an information processing device, such as a PC, a server device, or the like. Alternatively, the training device 500 may be implemented by a cloud system that performs the processes with one or a plurality of information processing devices connected via a network.

The processing section 510 is a processor such as a CPU, and the storage section 520 is a storage device such as a semiconductor memory, a hard disc drive, or the like. The storage section 520 stores a training model 522 and training data 521. The training data 521 herein includes first training data 521A, second training data 521B, and third training data 521C. In addition, the training model 522 includes a first training model 522A, a second training model 522B, and a third training model 522C. Then, the processing section 510 uses the training data 521 to train the training model 522 to generate a trained model 121. The training data 521 includes image data of a plurality of training images and training information regarding the energy output setting of the energy device 310. Further, correct answer data is added to the training images and the training information, respectively. The first training data 521A herein refers to training data associated with the energy device 310. In addition, the second training data 521B refers to training data associated with the biological tissue and the third training data 521C refers to training data associated with the remaining heat information. Further, the first training model 522A refers to a training model associated with the energy device 310, the second training model 522B refers to a training model associated with the biological tissue, and the third training model 522C refers to a training model associated with the remaining heat information. The training images described above include treatment images in which one or a plurality of biological tissues and one or a plurality of energy devices 310 are captured. Such a treatment image is also referred to as a training device tissue image. The training images may also include a treatment image in which one or a plurality of biological tissues are captured and no energy device 310 is captured. Such a treatment image is also referred to as a training tissue image. The correct answer data are annotations in the segmentation (region detection), annotations in the detection (location detection), correct answer labels in the classification (classification), or correct answer labels in the regression (regression analysis). The processing section 510 inputs training images to an inference process by the training model 522, and provides feedback to the training model 522 based on the error between the results of the inference process and the correct answer data. The processing section 510 repeats this process with a large number of training data to generate the trained model 121. Then, the trained model 121 thus generated is transferred to the storage section 120 of the controller 100.

Figure 14:
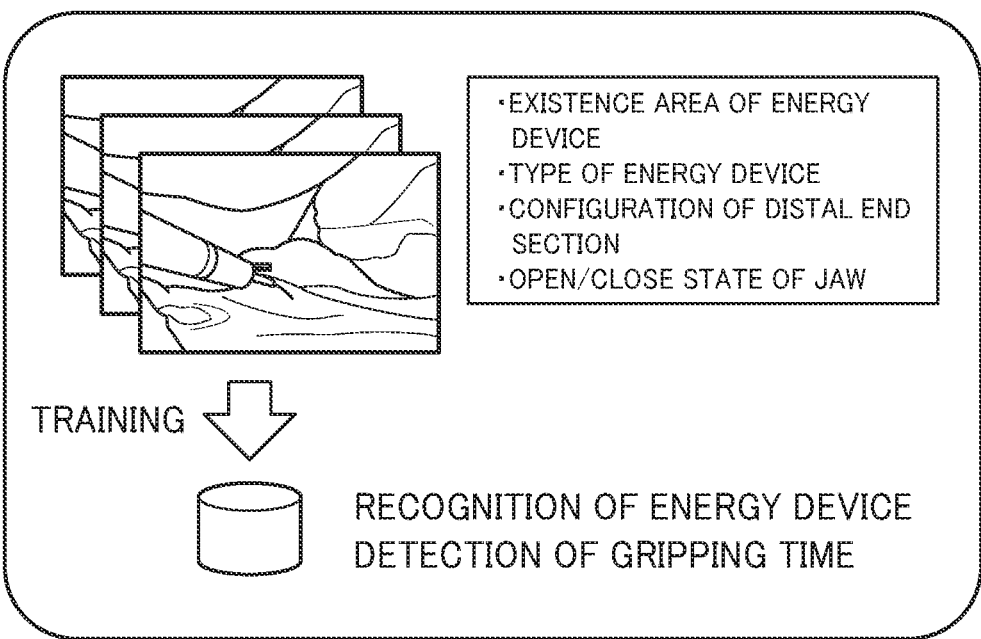
FIG. 14 is a diagram illustrating a training phase for estimation of an energy device.
Figure 15:
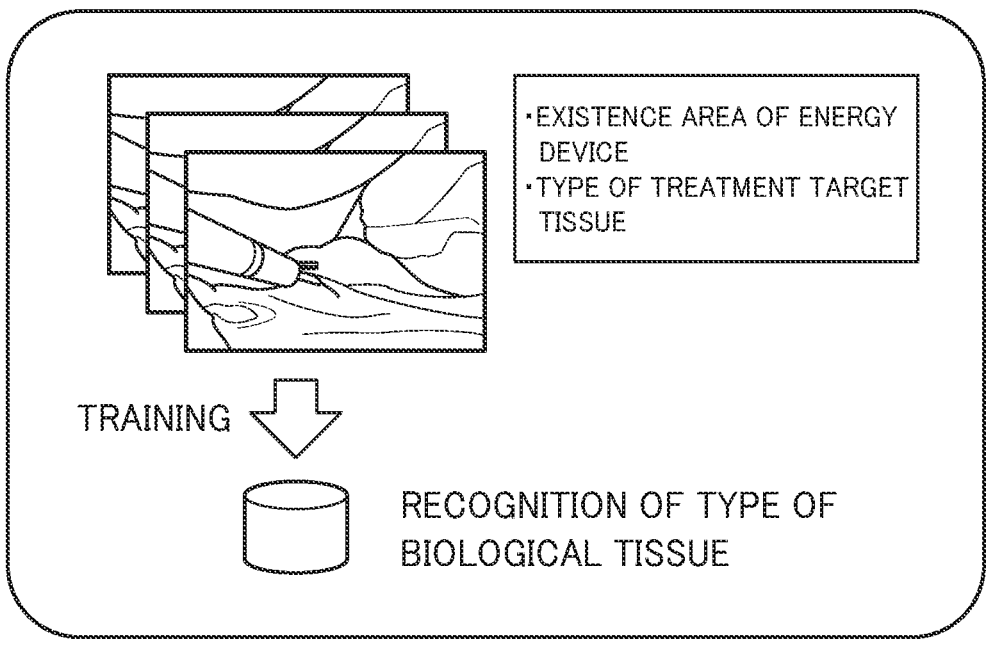
FIG. 15 is a diagram illustrating a training phase for estimation of a type of a biological tissue.
Figure 16:
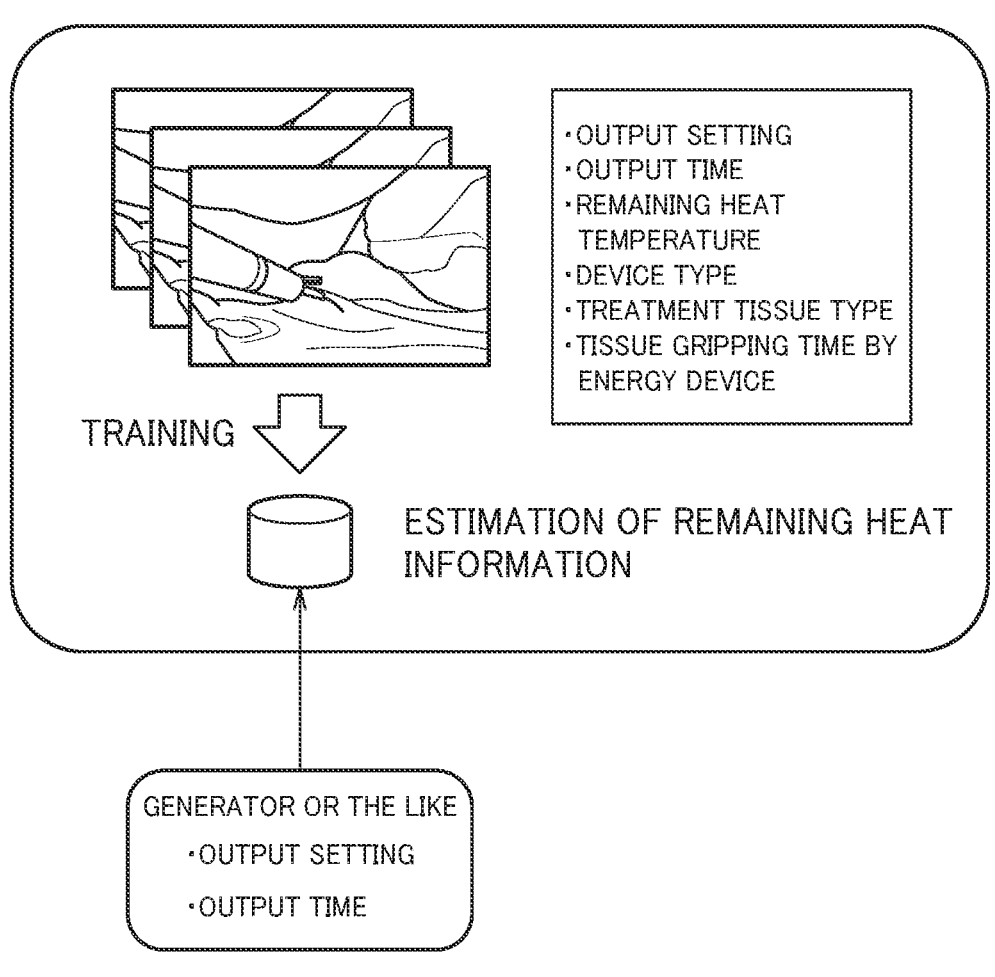
FIG. 16 is a diagram illustrating a training phase for estimation of remaining heat information.

FIGS. 14-16 are diagrams illustrating details of the training phase described above. FIG. 14 is a diagram illustrating the first trained model 122 used for estimation of the energy device 310 and the gripping time of the biological tissue in the first recognition section 111. As illustrated in FIG. 14, the training device 500 (not shown) provides feedback on the first training data 521A labeled with annotation corresponding to the treatment image, in which the energy device 310 and the biological tissue are captured, to the first training model 522A, thereby modifying the existing first trained model 122 and sending the new first trained model 122 to the controller 100. The contents of the annotation are information corresponding to the correct answer data including the type and position of the energy device 310, the configuration and condition of the distal end section of the energy device 310, the type of the biological tissue to be treated, or the like.

FIG. 15 is a diagram illustrating the second trained model 123 used for estimation of the type of the biological tissue in the second recognition section 112. As illustrated in FIG. 15, the training device 500 (not shown) provides feedback on the second training data 521B labeled with annotation corresponding to the treatment image to the second training model 522B, thereby modifying the existing second trained model 123 and sending the new second trained model 123 to the controller 100. The contents of the annotation are information corresponding to the correct answer data including the position of the energy device 310, the type of the biological tissue to be treated, or the like.

FIG. 16 is a diagram illustrating the third trained model 124 used for estimation of the remaining heat information in the estimation section 113. As illustrated in FIG. 16, the training device 500 (not shown) provides feedback on the third training data 521C labeled with annotation corresponding to the treatment image to the third training model 522C, thereby modifying the existing third trained model 124 and sending the new third trained model 124 to the controller 100. Note that, in the training phase, the estimation section 113 may be trained to estimate the temperature during energy supply.

The correct answer data added to the training images includes the type of the energy device 310, the remaining heat temperature of the distal end section of the energy device 310, the type of the biological tissue to be treated, the gripping time of the biological tissue, or the like. The remaining heat temperature obtained by a thermo-camera or a temperature sensor installed in the distal end of the treatment tool can be used for the correct answer data added to the training images. For example, color indicating the temperature is added to each site of the energy device 310 in an image captured by the thermo-camera. Then, the image is used as the training image for the third training data 521C, and the remaining heat information indicated by color in the image is used as the correct answer data. Note that the correct answer data may be added by a doctor, for example.

The correct answer label added to the training information regarding the energy output setting is, for example, information regarding the amount, time or the like of energy output, or the history thereof. The correct answer data added to the training information can be obtained from an instrument such as the generator 300. History information of the output energy may also be obtained from an instrument such as the generator 300. By providing feedback on the history information to the third training model 522C to generate the third trained model 124, it is possible to improve the estimation precision of the remaining heat information. In this manner, by providing feedback on numerous training device tissue images or training tissue images as the training data 521 to the training model 522, it is possible to enhance the estimation precision of the control section 110.

When performing energy treatment in surgery, it is important to protect a biological tissue from heat of an energy device and perform surgery efficiently while maintaining safety. When using an energy device in surgery, it is often difficult for non-experts to predict a remaining heat condition of the distal end section of the energy device, such as an active blade, a pad, or a shaft. For example, when continuously performing a series of treatments, the temperature of the energy device will gradually increase, but it is difficult to predict how hot it is now. In addition, especially with the ultrasonic device 340 in FIG. 6 described above, the temperature rises to about 200 degrees Celsius in a short period of time, making it difficult for a non-expert doctor to perform surgery efficiently while maintaining safety, which requires skill.

The medical device disclosed in U.S. Patent Application Publication No. 2018/0160910 displays presence or absence of a hot energy device on a treatment image when there is the energy device in a state of high temperature in the treatment image after using an energy treatment tool, and displays a warning image superimposed on the energy device in the image. However, the medical device does not present a specific remaining heat temperature in the treatment image, thus incapable of addressing different timing of cooling the energy device by each doctor. In addition, there is a problem that use of a thermo-camera or the like for temperature measurement leads to increased number of ports and increased thickness of a device with the sensor in a laparoscopic surgery. For example, a doctor reduces the temperature of the device by air cooling or putting the distal end section of the energy device on wet gauze, but it is difficult to adjust the degree thereof.

As a result, in some embodiments, the control section 110 estimates and presents to a doctor the remaining heat information such as a temperature through machine learning using, as training data, transition of the remaining heat temperature of the distal end section of the energy device 310 according to the time and amount of energization from a power supply to the energy device 310 as well as the type and condition of the treatment target tissue. For example, the machine learning is performed to estimate the current temperature of the energy device based on energy supplied to a given biological tissue. In this manner, it is possible to estimate and display in real time the remaining heat information of the distal end section of the energy device 310. This makes it possible to determine the timing of cooling the energy device 310 independent of experience and ability of a doctor. Therefore, even a non-expert doctor can easily avoid thermal injury to a spared tissue and perform the surgery more safely and efficiently.

5. Second Embodiment

In the second embodiment, the control section 110 uses transition of an amount of heat or a temperature after completion of energy output by the energy device 310 as the estimated remaining heat information, and causes the notification section 230 to make a notification based thereon. In other words, in the second embodiment, after completion of energy supply from the energy device 310, the estimation program described above estimates the transition of the amount of heat or the temperature of the distal end section of the energy device 310.

In the second embodiment, the trained model 121 is trained by a relationship of the training images and the training information to the transition of the remaining heat after energy output to estimate the transition of the amount of heat or the temperature after completion of the energy output. In other words, to generate the third trained model 124 that estimates the transition of the temperature of the energy device 310 after completion of the energy output, the training device 500 uses, as the third training data 521C, remaining heat history information during energy supply to modify the third trained model 124 to generate the new third trained model 124. Then, the estimation section 113 estimates the remaining heat information based on the third trained model 124 as described above. In this case, the estimation section 113 estimates the transition of the amount of heat or the temperature of the distal end of the energy device 310 after completion of the energy output based on the third training data 521C that is the information indicative of the type of the biological tissue, the gripping time of the biological tissue, the amount of energy output from the energy device 310, the output time, or the like.

Figure 17:
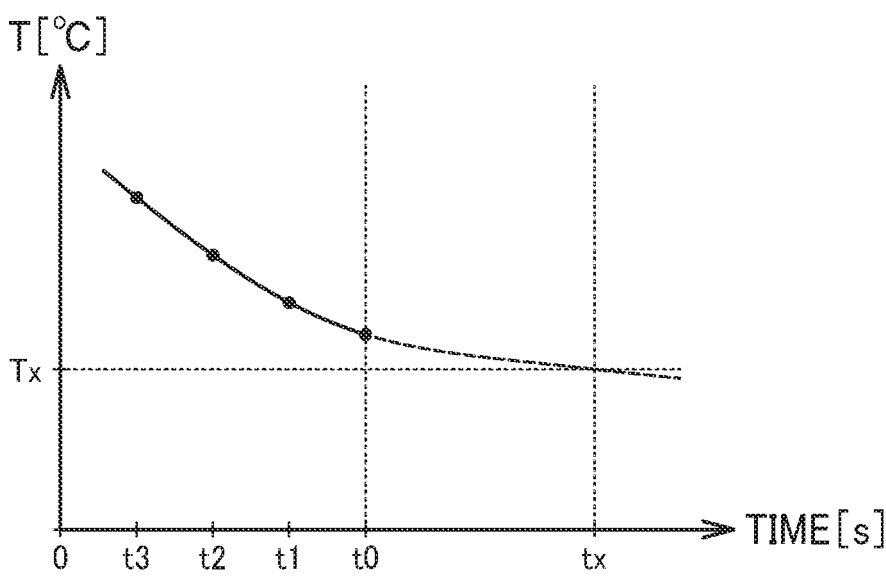
FIG. 17 is a diagram describing time dependency of a temperature of an energy device.

FIG. 17 is a diagram illustrating estimation of the transition of the temperature of the distal end section of the energy device 310. The horizontal axis is time (s) and the vertical axis is temperature (° C.). In addition, the relationship between each time is represented by t3<t2<t1<t0, and the current time is t0. In this case, if the temperatures at the time t3, t2, and t1 have been obtained at the time t0, the graph would be plotted with circles, as shown in FIG. 17, for example. Then, an approximate curve indicating time dependency of the remaining heat temperature can be obtained from these data. The approximate curve can be obtained using, for example, an analysis function of a computer. Furthermore, by extrapolating the approximate curve to the range of t>t0, as illustrated by the dashed line in FIG. 17, it is possible to estimate the transition of the amount of heat or the temperature after completion of the energy output by the energy device 310.

In this manner, a doctor can obtain not only the remaining heat information at the present time, but also information regarding the future transition of the temperature. Accordingly, the doctor can smoothly perform surgery.

Further, it is possible to estimate time till the temperature of the distal end section of the energy device 310 reaches a desired specified value based on the estimated transition of the temperature, and cause the notification section 230 to notify the estimated time. In other words, for example, when the temperature Tx, which may cause thermal injury to the biological tissue, is set to be the threshold, it is possible to present the time to give an indication of how much time must elapse from the current time t0 before the temperature falls below the threshold Tx so as to resume the treatment. The criterion for determining the presence or absence of thermal injury is based on, for example, whether or not protein denaturation or intracellular enzyme inactivation occurs. Though the threshold Tx of such temperature varies depending on the type of the biological tissue to be treated, it is, for example, from 50 to 60 degrees Celsius. When changing the desired specified value according to the type of the biological tissue to be treated, for example, a biological tissue with a high risk of thermal injury, such as a pancreas and a duodenum, it is possible to set the specified value lower to avoid the occurrence of thermal injury especially in a critical biological tissue. In the graph shown in FIG. 17, if the temperature at the desired specified value is the threshold Tx, the temperature of the distal end section of the energy device 310 reaches the threshold Tx at the time tx when the curve of the estimated transition of the temperature intersects T=Tx. Accordingly, the control section 110 obtains the time determined by tx−t0 and causes the notification section 230 to notify the time, thereby making it possible to present to a doctor an indication of how much more time must elapse before he/she can safely resume the treatment. In this manner, the doctor can know specifically how much time will be required before he/she can resume the treatment.

6. Third Embodiment

In the third embodiment, the control section 110 causes the notification section 230 to notify an alert when the amount of heat or the temperature of the energy device 310 estimated as the estimated remaining heat information is more than the threshold. In other words, in the present embodiment, the control section 110 estimates, for example, the temperature of the distal end section of the energy device 310, and when the estimated temperature is more than a predetermined threshold, notifies an alert to a doctor. The predetermined threshold is, for example, the threshold Tx that may cause thermal injury to the biological tissue as described in the section "5. Second Embodiment". In addition, the threshold may be determined as a value of the amount of heat of the distal end section of the energy device 310. If the temperature itself of the distal end section of the energy device 310 is low but the amount of heat is large, there may be a higher risk of thermal injury to the biological tissue due to heat imparted in a long period of time. Therefore, a doctor can select depending on the situation whether to specify the amount of heat by the threshold or the temperature.

The alert of the notification section 230 includes, for example, warning display on the display section 232 of the notification section 230. The display section 232 herein is, for example, a display of a personal computer. In other words, it is displayed on the display that the temperature of the distal end section of the energy device 310 exceeds the threshold to warn a doctor. In addition, upon warning, superimposed display on the energy device 310 displayed on the display section 232 may be performed by coloring a region exceeding the threshold in the treatment image. Further, as an aspect of the display on the display section 232, the control section 110 may cause displaying of the estimation result when the amount of heat or the temperature as the estimated remaining heat information is higher than the predetermined threshold.

Figure 18:
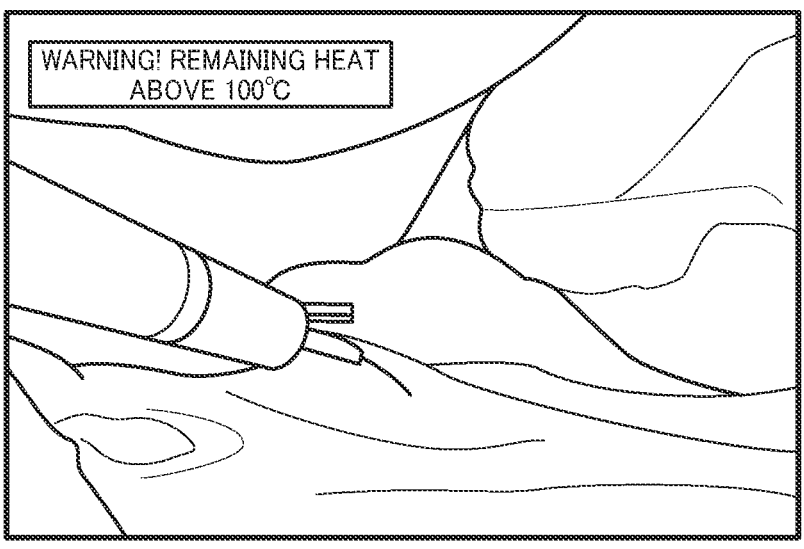
FIG. 18 is an example of alert display by a notification section.
Figures 19, 20:
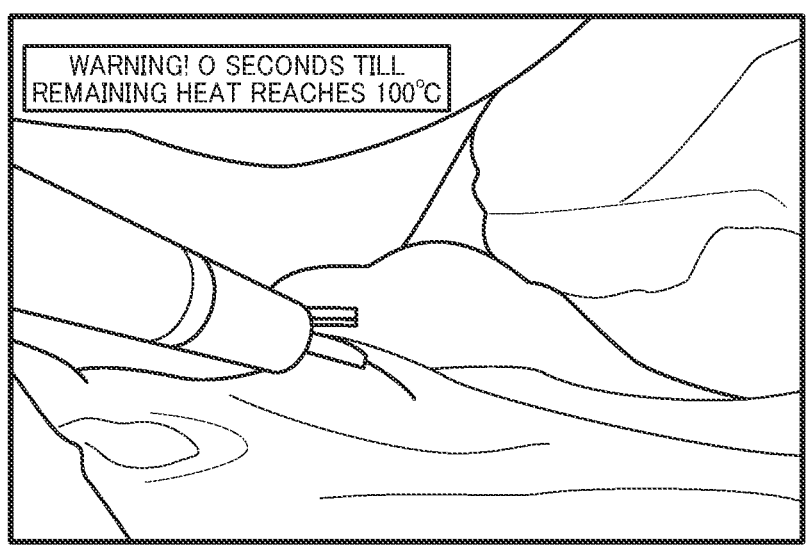
FIG. 19 is an example of alert display by a notification section.
FIG. 20 is a diagram illustrating processing in the case of notifying an alert.

The warning display can be displayed by adding, for example, a caption to the estimation results on a display screen as described above with reference to FIGS. 9-11. Specifically, the display examples shown in FIGS. 18 and 19 are possible. In the example shown in FIG. 18, a caption of "Warning! Remaining heat above 100° C." is displayed in the upper left of the image to warn a doctor that the temperature of the distal end section of the energy device 310 may cause thermal injury to the biological tissue. The example shown in FIG. 19 illustrates a case of displaying a caption of "Warning! O seconds till remaining heat reaches 100° C.". The display method shown in FIG. 19 is different from that shown in FIG. 18, displaying, for example, the time required for the temperature to fall below the aforementioned threshold temperature. Therefore, more useful information to proceed the surgery can be provided to a doctor to smoothly perform the surgery. The required time as described above can be obtained, for example, by the method of estimating the transition of the temperature of the distal end section of the energy device 310 as described in FIG. 17. Further, in the display shown in FIGS. 18 and 19, for example, the aforementioned caption can be displayed by blinking or the like to more effectively alert a doctor. Note that the warning is not limited to the display on the display section 232, but may be an alarm sound or a warning by vibration of the energy device 310, for example.

FIG. 20 is a diagram illustrating processing performed by the controller 100 or the like in the third embodiment. In the present embodiment, when the estimation section 113 of the control section 110 estimates that the temperature or the amount of heat of the distal end section of the energy device 310 is more than the threshold, the notification section 230 notifies the alert. On the other hand, when the amount of heat or the temperature of the distal end section of the energy device 310 is estimated to be equal to or less than the threshold, the notification section 230 does not notify the alert. In other words, when the amount of heat or the temperature of the distal end section of the energy device 310 exceeds the threshold after completion of energy supply by the energy device 310, for example, after turning off the energy device 310, the alert is to be notified. Here, in a case where the transition of the amount of heat or the temperature is estimated, notification of the alert is stopped after the amount of heat or the temperature becomes equal to or less than the threshold. In the above processing, for example, the storage section 120 stores table data of the remaining heat information and the control section 110 refers to the table data to output the process of the notification section 230 corresponding to the estimation result through the I/O device 190 to the notification section 230. Then, the notification section 230 operates according to the output result of the control section 110. Note that algorithm for notifying an alert is not limited to the above. According to the third embodiment, a doctor can recognize the remaining heat temperature of the distal end section of the energy device 310 to perform the surgery more safely and efficiently.

Furthermore, the system according to the present embodiment can also be implemented by a program. In other words, the program according to the present embodiment acquires at least one treatment image including an image in which at least one energy device 310 and at least one biological tissue are captured. Then, the program acquires the information regarding the amount of energy supply, that is the information regarding the energy output setting of the energy device 310, by processing based on the trained model 121 that is trained to output, from a training device tissue image, in which at least one energy device 310 that receives energy supply to output energy and at least one biological tissue are captured, or a training tissue image, in which at least one biological tissue is captured, the remaining heat information regarding the amount of heat remaining in the energy device 310 or the temperature thereof after energy is supplied to the energy device 310. Then, the program causes a computer to execute estimating, based on the treatment image, the information regarding the amount of energy supply, and the trained model 121, the estimated remaining heat information regarding the amount of heat or the temperature of the energy device 310, and displaying the estimated remaining heat information on the display section 232. The computer herein is assumed to be a network terminal such as a personal computer or the like. However, the computer may be a smart phone, a tablet terminal, or a wearable terminal such as a smart watch. In this manner, similar effect to the above can be obtained.

Further, the system according to the present embodiment can be implemented as an image processing method. In other words, the image processing method includes acquiring at least one treatment image including an image in which at least one energy device and at least one biological tissue are captured. Further, the method includes, acquiring information regarding the amount of energy supply, that is the information regarding the energy output setting of the energy device 310 by processing based on the trained model 121 that is trained to output, from a training device tissue image, in which at least one energy device 310 that receives energy supply to output energy and at least one biological tissue are captured, or a training tissue image, in which at least one biological tissue is captured, the remaining heat information regarding the amount of heat remaining in the energy device 310 or the temperature thereof after energy is supplied to the energy device 310. Then, the method includes estimating, based on the treatment image, the information regarding the amount of energy supply, and the trained model 121, the estimated remaining heat information regarding the amount of heat or the temperature of the energy device 310. In this manner, similar effect to the above can be obtained.

The system 10 according to the present embodiment described above includes the storage section 120 configured to store the trained model 121, and the control section 110. The trained model 121 is trained to output, from the training device tissue image, the training tissue image, and training information, the remaining heat information regarding the amount of heat remaining in the energy device 310 or the temperature thereof after energy is supplied to the energy device 310. The training device tissue image is an image in which at least one energy device 310 that receives energy supply to output energy and at least one biological tissue are captured. The training tissue image is an image in which at least one biological tissue is captured. The training information is the information regarding the amount of energy supply, which is regarding the energy output setting of the energy device. The control section 110 acquires at least one treatment image including an image in which at least one energy device 310 and at least one biological tissue are captured. The control section 110 acquires the information regarding the amount of energy supply, the information regarding the energy output setting of the energy device. The control section 110 estimates, based on the treatment image, the information regarding the amount of energy supply, and the trained model 121, the estimated remaining heat information regarding the amount of heat or the temperature of the energy device 310. The control section 110 causes the notification section to make a notification based on the estimated remaining heat information.

As a result, in some embodiments, it is possible to estimate and present to a doctor the remaining heat information such as a temperature through machine learning using, as the training data 521, the transition of the remaining heat temperature of the distal end section of the energy device 310 according to the time and amount of energization from the power supply to the energy device 310 as well as the type and condition of the treatment target tissue. In this manner, it is possible to estimate and display in real time the remaining heat information of the distal end section of the energy device 310. This makes it possible to determine the timing of cooling the energy device 310 independent of experience and ability of a doctor. Therefore, even a non-expert doctor can avoid thermal injury to a spared tissue and perform surgery more safely and efficiently. Note that the training device tissue image, the training tissue image, and the training information are described in the section "4. First Embodiment".

Further, in the present embodiment, the control section 110 may extract, from the treatment image, the tissue information regarding the biological tissue captured in the treatment image, and estimate, based on the tissue information and the information regarding the amount of energy supply, the estimated remaining heat information.

As a result, in some embodiments, the control section 110 can estimate the type of the biological tissue from the treatment image acquired by the endoscope system 200. Note that the treatment image is described in FIG. 8. In addition, the training phase for estimation of the biological tissue is described in the section "4. First Embodiment".

Further, in the present embodiment, the control section 110 may extract, from the treatment image, the device information regarding the energy device captured in the treatment image, estimate the treatment target tissue to be treated by the energy device based on the device information and the tissue information, and estimate the estimated remaining heat information based on the treatment target tissue.

As a result, in some embodiments, the control section 110 can estimate the device information regarding the energy device 310 from the treatment image acquired by the endoscope system 200, and estimate the remaining heat information of the energy device 310 based on the device information and the estimated tissue information. Note that the treatment image is described in FIG. 8. In addition, the training phase for estimation of the biological tissue is described in the section "4. First Embodiment".

Further, in the present embodiment, the control section 110 may estimate, as the estimated remaining heat information, the transition of the amount of heat or the temperature after completion of energy output by the energy device 310.

As a result, in some embodiments, a doctor can obtain not only the remaining heat information at the present time, but also the information regarding future transition of the temperature. Note that the method for estimating the transition of the amount of heat or the temperature is described in the section "5. Second Embodiment" with reference to FIG. 17.

Further, in the present embodiment, the trained model 121 may be the trained model 121 trained by the relationship of the training device tissue image or the training tissue image and the training information to the transition of the remaining heat after energy output so as to estimate the transition of the amount of heat or the temperature after completion of the energy output.

As a result, in some embodiments, based on the trained model 121 trained by the relationship of the training images and the training information to the transition of the remaining heat after energy output, the control section 110 can estimate the transition of the amount of heat or the temperature of the distal end of the energy device 310 after completion of the energy output. The details are described in the section "5. Second Embodiment".

Further, in the present embodiment, the control section 110 may estimate, as the estimated remaining heat information, the time till the amount of heat or the temperature of the energy device 310 reaches a desired specified value after completion of energy output by the energy device 310.

As a result, in some embodiments, a doctor can set a desired amount of heat or the like and know the specific time required for the energy device 310 to obtain the amount of heat or the like. Accordingly, it is possible to smoothly perform surgery. The details are described in the section "5. Second Embodiment".

Further, in the present embodiment, the control section 110 may cause the notification section to notify the alert when the amount of heat or the temperature of the energy device 310, which is estimated as the estimated remaining heat information, is more than the predetermined threshold.

As a result, in some embodiments, by setting the threshold which is a temperature that may cause thermal injury to a biological tissue, a doctor can recognize a thermal injury risk to the biological tissue due to the remaining heat of the distal end section of the energy device 310. Accordingly, it is possible to perform surgery more safely and efficiently. The notification method of the alert is described in the section "6. Third Embodiment" with reference to FIG. 20. Further, in the present embodiment, the notification section 230 is the display section 232 and the control section 110 may cause the display section 232 to display the estimated remaining heat information.

As a result, in some embodiments, the amount of heat, the temperature, or the time till the amount of heat or the temperature of the energy device 310 reaches a desired specified value is displayed on the display section 232, thereby allowing a doctor to determine whether or not to wait until the temperature of the energy device 310 decreases. The details are described in the section "4. First Embodiment" with reference to FIGS. 9-12.

Further, in the present embodiment, the control section 110 may cause the display section to display the amount of heat or the temperature of the energy device, which is estimated as the estimated remaining heat information, when the amount of heat or the temperature of the energy device 310 estimated as the remaining heat information is more than the threshold.

As a result, in some embodiments, a doctor can recognize, based on the display on the display section 232, whether or not thermal injury to the biological tissue will occur due to the remaining heat of the distal end section of the energy device 310. Accordingly, it allows a doctor to perform surgery more safely and efficiently. The details are described in the section "6. Third Embodiment".

Further, in the present embodiment, the control section 110 may cause superimposed display of color indicating the amount of heat or the temperature of the energy device 310, which is estimated as the estimated remaining heat information, on the energy device 310 displayed on the display section 232.

As a result, in some embodiments, the energy device 310 may be a bipolar device 330. The details are described in the section "4. First Embodiment" with reference to FIGS. 9-12.

Further, the above processing may also be written as a program. Specifically, the program of the present embodiment causes the controller 100 to: acquire a treatment image; acquire information regarding the amount of energy supply by processing based on the trained model 121; estimate the estimated remaining heat information based on the treatment image, the information regarding the amount of energy supply, and the trained model 121; and display the estimated remaining heat information on the display section 232.

Further, the above processing may also be written as a method. Specifically, the method of the present embodiment includes acquiring a treatment image, acquiring information regarding the amount of energy supply by processing based on the trained model 121, and estimating the estimated remaining heat information based on the treatment image, the information regarding the amount of energy supply, and the trained model 121.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. A system comprising:
a memory storing a model that is trained based on:
    a plurality of images that captured at least one of an energy device and at least one biological tissue; and
    at least one of an energy output setting of the energy device and a temperature of the energy device after energy is supplied to the energy device; and
a processor,
wherein the processor:
    acquires an endoscope image during a treatment that utilizes the energy device, wherein the endoscope image captures the energy device and the at least one biological tissue,
    acquires information regarding an energy output setting of the energy device during the treatment, runs the model, with the endoscope image and the acquired information as input, to estimate a temperature of the energy device after completion of energy output by the energy device during the treatment,
    generates a notification based on the estimated temperature of the energy device, and
    outputs the generated notification to indicate an alert regarding the estimated temperature of the energy device.

2. The system as defined in claim 1,
wherein the processor:
    extracts, from the endoscope image, information regarding a biological tissue that is captured in the endoscope image, and
    runs the model to estimate the temperature of the energy device based on the information regarding the biological tissue and the acquired information regarding the energy output setting of the energy device during the treatment.

3. The system as defined in claim 2,
wherein the processor:
    extracts, from the endoscope image, information regarding the energy device that is captured in the endoscope image, and
    runs the model to estimate the temperature of the energy device based on the information regarding the energy device and the information regarding the biological tissue.

4. The system as defined in claim 1,
wherein the model is trained based on a relationship among the plurality of images, the energy output setting of the energy device, and the temperature of the energy device after energy is supplied to the energy device.

5. The system as defined in claim 4,
wherein the processor runs the model to estimate a time for the temperature of the energy device to reach a specified value after the completion of energy output by the energy device.

6. The system as defined in claim 1,
wherein the alert indicates the estimated temperature of the energy device is higher than a predetermined threshold.

7. The system as defined in claim 1, wherein:
the processor outputs the generated notification on a display to display the estimated temperature of the energy device.

8. The system as defined in claim 7,
wherein the processor outputs the generated notification on the display when the estimated temperature of the energy device is higher than a predetermined threshold.

9. The system as defined in claim 7,
wherein the processor superimposes color on the display to indicate the estimated temperature of the energy device.

10. A computer-readable non-transitory information storage medium storing a program for causing a computer to execute:
    acquiring an endoscope image during a treatment that utilizes an energy device, wherein the endoscope image captures the energy device and at least one biological tissue;
    acquiring information regarding an energy output setting of the energy device during the treatment;
    running a model, with the endoscope image and the acquired information as input, to estimate a temperature of the energy device after completion of energy output by the energy device during the treatment, wherein the model is trained based on:

a plurality of images that captured at least one of an energy device and at least one biological tissue; and at least one of energy output setting of the energy device and a temperature of the energy device after energy is supplied to the energy device; and displaying the estimated temperature of the energy device on a monitor.

11. The computer-readable non-transitory information storage medium as defined in claim 10, which stores the program for causing the computer to execute:

extracting, from the endoscope image, information regarding a biological tissue that is captured in the endoscope image, and running the model to estimate the temperature of the energy device based on the information regarding the biological tissue and the acquired information regarding the energy output setting of the energy device during the treatment.

12. The computer-readable non-transitory information storage medium as defined in claim 10, wherein the model is trained based on a relationship among the plurality of images, the energy output setting of the energy device, and the temperature of the energy device after energy is supplied to the energy device.

13. The computer-readable non-transitory information storage medium as defined in claim 12, which stores the program for causing the computer to execute:

running the model to estimate a time for the temperature of the energy device to reach a specified value after completion of the energy output by the energy device.

14. An information processing method, comprising:

acquiring an endoscope image during a treatment that utilizes an energy device, wherein the endoscope image captures energy device and at least one biological tissue;

acquiring information regarding an energy output setting of the energy device during the treatment;

running a model, with the endoscope image and the acquired information as input, to estimate a temperature of the energy device after completion of energy output by the energy device during the treatment, wherein the model is trained based on:

a plurality of images that captured at least one of an energy device and at least one biological tissue; and at least one of energy output setting of the energy device and a temperature of the energy device after energy is supplied to the energy device; and displaying the estimated temperature of the energy device on a monitor.

15. The information processing method as defined in claim 14, comprising:

extracting, from the endoscope image, information regarding a biological tissue that is captured in the endoscope image; and running the model to estimate the temperature of the energy device based on the information regarding the biological tissue and the acquired information regarding the energy output setting of the energy device during the treatment.

16. The information processing method as defined in claim 14, wherein the model is trained based on a relationship among the plurality of images, the energy output setting of the energy device, and the temperature of the energy device after energy is supplied to the energy device.

17. The information processing method as defined in claim 16, comprising running the model to estimate a time for the temperature of the energy device to reach a specified value after completion of the energy output by the energy device.

* * * * *